(12) United States Patent
Yasukawa et al.

(10) Patent No.: US 8,900,814 B2
(45) Date of Patent: Dec. 2, 2014

(54) VARIANT REVERSE TRANSCRIPTASE

(75) Inventors: Kiyoshi Yasukawa, Kyoto (JP); Kuniyo Inouye, Kyoto (JP)

(73) Assignee: Kyoto University, Kyoto-shi, Kyoto (JP)

( * ) Notice: Subject to any disclaimer, the term of this patent is extended or adjusted under 35 U.S.C. 154(b) by 0 days.

(21) Appl. No.: 13/816,497

(22) PCT Filed: Aug. 9, 2011

(86) PCT No.: PCT/JP2011/068157
§ 371 (c)(1),
(2), (4) Date: Feb. 12, 2013

(87) PCT Pub. No.: WO2012/020759
PCT Pub. Date: Feb. 16, 2012

(65) Prior Publication Data
US 2013/0143225 A1 Jun. 6, 2013

(30) Foreign Application Priority Data
Aug. 13, 2010 (JP) ................................. 2010-181471

(51) Int. Cl.
*C12N 9/12* (2006.01)
*C12N 15/10* (2006.01)
(52) U.S. Cl.
CPC ....... *C12N 9/1276* (2013.01); *C12Y 207/07049* (2013.01); *C12N 15/1096* (2013.01)
USPC ....... 435/6.12; 435/194; 435/91.21; 536/23.2
(58) Field of Classification Search
None
See application file for complete search history.

(56) References Cited

U.S. PATENT DOCUMENTS

2008/0227661 A1* 9/2008 Hogrefe et al. ................. 506/26

FOREIGN PATENT DOCUMENTS

| JP | 2004-511211 | 4/2004 |
|----|-------------|--------|
| JP | 2009-504162 | 2/2009 |
| WO | WO 01/92500 | 12/2001 |
| WO | 2009/125006 A2 | 10/2009 |

OTHER PUBLICATIONS

Yasukawa et al. "Increase in thermal stability of Moloney murine lukaemia virus reverse transcriptase by site-directed mutagenesis" 2010 Journal of Biotechnology 150 299-306.*
International Search Report for corresponding International Application No. PCT/JP2011/068157, Nov. 15, 2011.
Arezi,B. et al., Novel mutations in Moloney Murine Leukemia Virus reverse transcriptase increase thermostability through tighter binding to template-primer, Nucleic Acids Res., 2009, p. 473-481, vol. 37, No. 2.
Mizuno,M. et al., Insight into the mechanism of the stabilization of moloney murine leukaemia virus reverse transcriptase by eliminating RNase H activity, Biosci.Biotechnol.Biochem., Feb. 7, 2010, p. 440-442, vol. 74, No. 2.
Yasukawa,K. et al., Increase in thermal stability of Moloney murine leukaemia virus reverse transcriptase by site-directed mutagenesis, J.Biotechnol., Oct. 8, 2010, p. 299-306, vol. 150, No. 3.
European Search Report for the corresponding European Patent Application No. 11816423.5, issued May 6, 2014, 8 pages.

* cited by examiner

*Primary Examiner* — Suzanne M Noakes
*Assistant Examiner* — Gerard Lacourciere
(74) *Attorney, Agent, or Firm* — Ditthavong & Steiner, PC

(57) ABSTRACT

The present invention provides a versatile mutant reverse transcriptase with high thermal stability, a nucleic acid thereof and a method for producing a mutant reverse transcriptase, a versatile kits for reverse transcription and detection, a method for improving thermal stability of a nucleic acid-related enzyme, which significantly improves thermal stability of a nucleic acid-related enzyme, and a reverse transcription method, which efficiently performs a reverse transcription. An amino acid residue in a nucleic acid interaction region of a wild-type enzyme is substituted with a positively-charged amino acid residue or a nonpolar amino acid residue, to form a nucleic acid interaction region having a positive effective charge larger than the nucleic acid interaction region of a wild-type enzyme.

12 Claims, 7 Drawing Sheets

VARIANT REVERSE TRANSCRIPTASE

TECHNICAL FIELD

The present invention relates to a mutant reverse transcriptase. More particularly, the present invention relates to a mutant reverse transcriptase, a nucleic acid encoding thereof, a reverse transcription method using the mutant reverse transcriptase, a kit for reverse transcription and a detection kit each containing the mutant reverse transcriptase, and a method for improving thermal stability of a nucleic acid-relating enzyme including the mutant reverse transcriptase and the like, which are useful for a genetic analysis, an examination for diseases, and the like.

BACKGROUND ART

Generally, a reverse transcriptase has an activity of synthesizing cDNA with the use of RNA as a template (hereinafter, referred to as "RNA dependent DNA polymerase activity"), an activity of synthesizing DNA with the use of DNA as a template (hereinafter, referred to as "DNA dependent DNA polymerase activity"), and an activity of degrading RNA strand in RNA:DNA hybrid (hereinafter, referred to as "RNase H activity").

The reverse transcriptase has been used in application including analysis of nucleotide sequence of mRNA which reflects an amino acid sequence of a protein expressed in a living body, construction of cDNA library, RT-PCR, and the like, since the reverse transcriptase has the RNA dependent DNA polymerase activity. Conventionally, Moloney murine leukaemia virus reverse transcriptase or avian myeloblastosis virus reverse transcriptase has been used for the application.

In addition, when mRNA has a nucleotide sequence likely to form secondary structure, cDNA synthesis by the reverse transcriptase is inhibited by the secondary structure. Therefore, it is desired that cDNA is synthesized while inhibiting formation of the secondary structure by elevating reaction temperature. However, since the Moloney murine leukaemia virus reverse transcriptase and the avian myeloblastosis virus reverse transcriptase have low thermal stability, the Moloney murine leukaemia virus reverse transcriptase and the avian myeloblastosis virus reverse transcriptase are sometimes inactivated at a temperature capable of inhibiting the formation of secondary structure of RNA. Therefore, a reverse transcriptase possessing improved thermal stability is proposed (for instance, see Patent Literature 1 and Non Patent Literature 1).

CITATION LIST

Patent Literature

Patent Literature 1: Japanese Unexamined Patent Application Publication No.: 2004-511211

Non Patent Literature

Non Patent Literature 1: Bahram Arezi et al., "Novel mutations in Moloney Murine Leukemia Virus reverse transcriptase increase thermostability through tighter binding to template-primer", Nucleic Acids Research, publication on 2009 (online publication date: Dec. 4, 2008), Vol. 37, pp. 473-481

SUMMARY OF INVENTION

Problems to be Solved by Invention

However, a reverse transcriptase having higher thermal stability and capable of performing a versatile reverse transcription is required.

The present invention has been made in view of the above prior art, and an object of the present invention is to a reverse transcriptase having higher thermal stability and high general versatility. In addition, an object of the present invention is to provide a nucleic acid and a method for producing the mutant reverse transcriptase, which can easily obtain the mutant reverse transcriptase. Furthermore, an object of the present invention is to provide a method for improving thermal stability of a nucleic acid-relating enzyme, which can significantly improve thermal stability of the nucleic acid-relating enzyme. Further, an object of the present invention is to provide a verstile reverse transcription method, which can effectively perform a reverse transcription.

Means for Solving the Problem

Specifically, the gist of the present invention is:
{1} a mutant reverse transcriptase comprising a DNA interaction region having a substitution of an amino acid residue in a DNA interaction region of a wild-type reverse transcriptase with a positively-charged amino acid residue or a nonpolar amino acid residue and having a positive effective charge larger than that of the DNA interaction region in the wild-type reverse transcriptase,
wherein the mutant reverse transcriptase exhibits a reverse transcriptase activity,
{2} the mutant reverse transcriptase according to the above item {1}, wherein the wild-type reverse transcriptase comprises an amino acid sequence corresponding to SEQ ID NO.: 2, and
wherein the amino acid residue in the DNA interaction region of the wild-type reverse transcriptase is an amino acid residue localized in a region corresponding to a threonine residue at position 24 to a proline residue at position 474 of SEQ ID NO.: 2,
{3} the mutant reverse transcriptase according to the above item {2}, wherein the mutant reverse transcriptase has a conserved substitution of an amino acid residue within a region corresponding to a threonine residue at position 24 to a proline residue at position 474 of SEQ ID NO.: 2, in an amino acid sequence corresponding to SEQ ID NO.: 2,
{4} the mutant reverse transcriptase according to the above item {2} or {3}, wherein the mutant reverse transcriptase comprises any one of amino acid sequences:
(A) an amino acid sequence further including substitution, deletion, insertion or addition of one or several amino acid residues within an amino acid sequence corresponding to SEQ ID NO.: 2 except for a region corresponding to a threonine residue at position 24 to a proline residue at position 474 of SEQ ID NO.: 2, and
(B) an amino acid sequence having at least 80% sequence identity, the sequence identity being obtained by aligning the amino acid sequence with a sequence except for a region corresponding to a threonine residue at position 24 to a proline residue at position 474 in SEQ ID NO.: 2, with the use of BLAST algorithm under conditions of Gap Costs (Existence 11 and Extension 1), Expect 10 and Word Size 3,
wherein the mutant reverse transcriptase exhibits a reverse transcriptase activity, {5} the mutant reverse transcriptase according to any one of the above items {2} to {4}, wherein at least one of negatively-charged amino acid residues among amino acid residues localized in a region corresponding to a threonine residue at position 24 to a proline residue at position 474 of SEQ ID NO.: 2 is substituted with a positively-charged amino acid residue or a nonpolar amino acid residue, {6} a mutant reverse transcriptase comprising an amino acid sequence having a substitution of an amino acid residue corresponding to at least a glutamate residue at position 286 of SEQ ID NO.: 2 with a positively-charged amino acid residue or a nonpolar amino acid residue, in an amino acid sequence corresponding to SEQ ID No. 2,
wherein the mutant reverse transcriptase exhibits a reverse transcriptase activity, {7} a mutant reverse transcriptase comprising an amino acid sequence having a substitution of a residue corresponding to at least one of amino acid residues:
a glutamate residue at position 69,
an aspartate residue at position 108,
a glutamate residue at position 117,
an aspartate residue at position 124,
a glutamate residue at position 286,
a glutamate residue at position 302,
a tryptophan residue at position 313,
a leusine residue at position 435, and
an asparagine residue at position 454,
in SEQ ID NO.: 2 with a positively-charged amino acid residue or a nonpolar amino acid residue, in an amino acid sequence corresponding to SEQ ID No.: 2, with proviso that substitution of a glutamate residue at position 302 with alginine is excluded,
wherein the mutant reverse transcriptase exhibits a reverse transcriptase activity, {8} a mutant reverse transcriptase characterized in that the mutant reverse transcriptase comprises an amino acid sequence having at least one substitution selected from the group consisting of the following amino acid residue substitutions (a) to (i):
(a) a substitution of a residue corresponding to a glutamate residue at position 286 of SEQ ID NO.: 2 with an alanine residue, a lysine residue or an arginine residue,
(b) a substitution of a residue corresponding to a glutamate residue at position 302 of SEQ ID NO.: 2 with an alanine residue or a lysine residue,
(c) a substitution of a residue corresponding to a leusine residue at position 435 of SEQ ID NO.: 2 with an alanine residue, a lysine residue or an arginine residue,
(d) a substitution of a residue corresponding to an aspartate residue at position 124 of SEQ ID NO.: 2 with an alanine residue, a lysine residue or an arginine residue,
(e) a substitution of a residue corresponding to a glutamate residue at position 69 of SEQ ID NO.: 2 with an alanine residue or an arginine residue,
(f) a substitution of a residue corresponding to an aspartate residue at position 108 of SEQ ID NO.: 2 with an alanine residue, a lysine residue or an arginine residue,
(g) a substitution of a residue corresponding to a glutamate residue at position 117 of SEQ ID NO.: 2 with an alanine residue or a lysine residue,
(h) a substitution of a residue corresponding to a tryptophan residue at position 313 of SEQ ID NO.: 2 with an alanine residue, a lysine residue or an arginine residue, and
(i) a substitution of a residue corresponding to an aspargine residue at position 454 of SEQ ID NO.: 2 with an alanine residue or an arginine residue,
in an amino acid sequence corresponding to SEQ ID NO.: 2,
wherein the mutant reverse transcriptase exhibits a reverse transcriptase activity, {9} the mutant reverse transcriptase according to the above item {8}, comprising:
(I) an amino acid sequence having the following amino acid residue substitutions (a-1) to (c-1):
(a-1) a substitution of a residue corresponding a glutamate residue at position 286 of SEQ ID NO.:2 with an alanine residue,
(b-1) a substitution of a residue corresponding a glutamate residue at position 302 of SEQ ID NO.:2 with a lysine residue, and
(c-1) a substitution of a residue corresponding a leusine residue at position 435 of SEQ ID NO.:2 with an arginine residue,
in an amino acid sequence corresponding to SEQ ID NO.:2,
or (II) an amino acid sequence further including the following substitution:
(d-1) a substitution of a residue corresponding to an asparagine residue at position 124 of SEQ ID NO.:2 with an arginine residue,
in the amino acid sequence of the item (I),
wherein the mutant reverse transcriptase exhibits a reverse transcriptase activity, {10} the mutant reverse transcriptase according to the above item {9}, comprising an amino acid sequence including the following substitution:
(e-1) a substitution of a residue corresponding to an aspartate residue at position 524 of SEQ ID NO.:2 with an alanine residue,
in the amino acid sequence of the item (I) or (II),
wherein the mutant reverse transcriptase exhibits a reverse transcriptase activity, {11} a nucleic acid encoding the mutant reverse transcriptase of any one of the above items {1} to {10}, {12} a method for producing the mutant reverse transcriptase of any one of the above items {1} to {10}, comprising the steps of:
culturing a cell harboring the nucleic acid of the above item {11} to express the reverse transcriptase encoded by the nucleic acid, thereby giving a culture, and
collecting the mutant reverse transcriptase from the culture obtained in the above step, {13} a method for reverse transcription, comprising synthesizing cDNA from RNA with the use of the mutant reverse transcriptase of any one of the above items {1} to {10}, {14} a kit for performing a reverse transcription, comprising the mutant reverse transcriptase of any one of the above items {1} to {10}, {15} a kit for detecting a marker in a sample containing RNA obtained from a living body, comprising the mutant reverse transcriptase of any one of the above items {1} to {10} and a reagent for detecting the marker, {16} a method for enhancing thermal stability of a nucleic-acid related enzyme having a nucleic acid interaction region which interacts with a nucleic acid, comprising introducing a mutation into a nucleotide sequence corresponding to a nucleic acid interaction region in a nucleic acid encoding a wild-type nucleic-acid related enzyme, to thereby form a nucleic acid interaction region having a positive effective charge larger than that of the nucleic acid interaction region in the wild-type nucleic-acid related enzyme, wherein the mutation is a substitution of an amino acid residue in the nucleic acid interaction region with a positively-charged amino acid residue or a nonpolar amino acid residue, {17} the method according to the above item {16}, wherein the nucleic-acid related enzyme is a reverse transcriptase.

Advantageous Effects of Invention

The mutant reverse transcriptase of the present invention has excellent properties such as high thermal stability and high general versatility. In addition, according to the nucleic acid and the method for producing a mutant reverse transcriptase of the present invention, the mutant reverse transcriptase can be easily obtained. Furthermore, the kit for reverse transcription and the detection kit of the present invention possess excellent properties such as high general versatility. Further, according to the method for improving thermal stability of a nucleic acid-relating enzyme of the present invention, thermal stability of a nucleic acid-relating enzyme can be significantly improved. In addition, the reverse transcription method of the present invention has high versatility, and according to the method, reverse transcription be can effectively performed.

DESCRIPTION OF EMBODIMENTS

Figure 1:
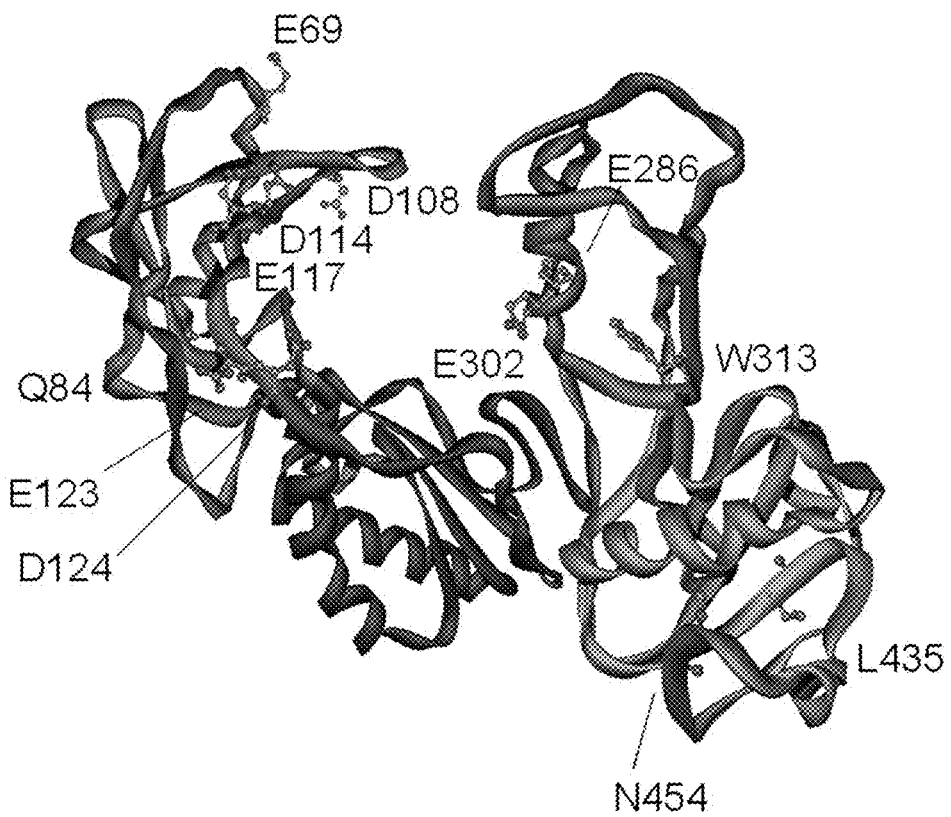
FIG. 1 is a drawing of ribbon model showing localization position of amino acid residues to be substituted which are selected in Production Example 2 in a wild-type MMLV reverse transcriptase.

The present inventors have found that thermal stability of a reverse transcriptase is significantly improved by introducing a positively-charged amino acid residue or a nonpolar amino acid residue into a DNA interaction region of a reverse transcriptase, to increase positive effective charge of a DNA interaction region of the resulting reverse transcriptase larger than that of a reverse transcriptase into which the amino acid residue is not introduced. The present invention is based on these findings.

1. Mutant Reverse Transcriptase

The mutant reverse transcriptase of the present invention is characterized in that the mutant reverse transcriptase has a DNA interaction region having a substitution of an amino acid residue in a DNA interaction region of a wild-type reverse transcriptase with a positively-charged amino acid residue or a nonpolar amino acid residue and has a positive effective charge larger than that of the DNA interaction region in the wild-type reverse transcriptase, wherein the mutant reverse transcriptase exhibits a reverse transcriptase activity.

Since the mutant reverse transcriptase of the present invention has the above DNA interaction region, the mutant reverse transcriptase exhibits high thermal stability. Thus, according to the mutant reverse transcriptase of the present invention, reverse transcription can be performed at high temperature. Accordingly, by elevating reaction temperature, cDNA can be synthesized while inhibiting formation of the secondary structure, whenever RNA has a nucleotide sequence likely to form secondary structure. Therefore, according to the mutant reverse transcriptase, versatile reverse transcription can be performed.

Here, in the present specification, the term "wild-type reverse transcriptase" refers to a reverse transcriptase into which mutation is not introduced artificially (hereinafter, also referred to as "WTRT"). The WTRT includes a reverse transcriptase consisting of amino acid sequence corresponding to SEQ ID NO.: 2, and the like. Here, "amino acid sequence corresponding to SEQ ID NO.: 2" refers to any of an amino acid sequence shown in SEQ ID NO.: 2 (Moloney murine leukaemia virus reverse transcriptase), and an amino acid sequence of ortholog of the reverse transcriptase consisting of the amino acid sequence shown in SEQ ID NO.: 2 (for instance, avian myeloblastosis virus reverse transcriptase, human immunodeficiency virus reverse transcriptase, and the like).

In addition, in the present specification, the term "mutant reverse transcriptase" refers to a reverse transcriptase into which mutation is artificially introduced. Further, "Moloney murine leukaemia virus reverse transcriptase" is designated as "MMLV reverse transcriptase".

Furthermore, in the present specification, "DNA interaction region" refers to a region in a reverse transcriptase, in which an amino acid residue interacting with DNA is localized.

In addition, in the present specification, the phrase "having a positive effective charge larger than that of the DNA interaction region in the wild-type reverse transcriptase" means that a positive effective charge at a pH suitable for performing the reverse transcription (for instance, a pH of 6.0 to 9.5) is larger than that of DNA interaction region in the wild-type reverse transcriptase at the same pH.

For example, when charge score of each of a lysine residue and an arginine residue which are positively-charged amino acid residues is defined as "+1" and charge score of each of an aspartate residue and a glutamate residue which are negatively-charged amino acid residues is defined as "−1", the magnitude of an effective charge can be calculated by using the formula (I):

$$\text{Score for magnitude of effective charge} = (+1 \times k) + (+1 \times r) + (-1 \times d) + (-1 \times e) \quad (I)$$

wherein k represents number of a lysine residue, r represents number of an arginine residue, d represents number of an aspartate residue, and e represents number of a glutamate residue, based on numbers of each of a lysine residue, an arginine residue, an aspartate residue and a glutamate residue contained in DNA interaction region.

It is desired that a positively-charged amino acid residue or a nonpolar amino acid residue is localized on the DNA interaction region of the mutant reverse transcriptase of the present invention so as to have a score of effective charge larger than a score (+7) of effective charge of the DNA interaction region of the wild-type MMLV reverse transcriptase. Usually, score of magnitude of effective charge of the DNA interaction region of the mutant reverse transcriptase of the present invention can be +8 to +13, preferably +9 to +13, more preferably +11 to +13, from the viewpoint of ensuring high thermal stability and high specific activity.

The positively-charged amino acid residue includes, for instance, an arginine residue, a lysine residue, a histidine residue, and the like. Among them, an arginine residue and a lysine residue are preferable, since the residues are positively-charged at a pH suitable for performing the reverse transcription (for instance, a pH of 6.0 to 9.5), and high thermal stability can be ensured under pH conditions of the pH ranges.

The nonpolar amino acid residue includes, for instance, an alanine residue, a glycine residue, a valine residue, a leucine residue, an isoleucine residue, a methionine residue, a cystein residue, a tryptophan residue, a phenylalanine residue, a proline residue, and the like. Among them, an alanine residue is preferable, since the residue has small size of side chain, and substitution with the residue is thought to cause small shape change.

The reverse transcriptase activity can be measured by carrying out the following steps (1) to (6):
(1) incubating a reverse transcriptase in a reaction solution {composition: 25 mM Tris-hydrochloride buffer (pH 8.3), 50 mM potassium chloride, 2 mM dithiothreitol, 5 mM magnesium chloride, 12.5 μM poly(rA)·p(dT)$_{15}$(p (dT)$_{15}$ converted concentration) and 0.2 mM [methyl-$^3$H]dTTP} at 37° C.,
(2) collecting the product obtained in the above step (1), and thereafter spotting on glass filter,
(3) repeating three times the manipulation including washing of the glass filter after the above step (2) for 10 minutes with 5% by mass of cold trichloroacetate aqueous solution and subsequent washing of the filter with 95% by mass of cold ethanol aqueous solution, thereby removing [$^3$H]dTTP unincorporated in poly(rA)·p(dT)$_{15}$ from the product on the glass filter,
(4) drying the glass filter after the above step (3), and thereafter putting the glass filter in 2.5 mL of a reagent for liquid scintillation to count radioactivity,
(5) calculating an amount of [$^3$H]dTTP incorporated in poly(rA)·p(dT)$_{15}$ (hereinafter, referred to as "amounts of dTTP incorporated") on the basis of the radioactivity obtained in the above step (4), and
(6) calculating an amount of reverse transcriptase incorporating 1 nmol of dTTP into poly(rA)·p(dT)$_{15}$ for 10 minutes on the basis of the amounts of dTTP incorporated calculated in the above step (5).

In the present invention, from the viewpoint of ensuring high thermal stability and ensuring sufficient specific activity, it is preferable that WTRT consists of an amino acid sequence corresponding to SEQ ID NO.: 2, and amino acid residues in the DNA interaction region of the WTRT are amino acid residues localized in a region corresponding to a threonine residue at position 24 to a proline residue at position 474 in SEQ ID NO.: 2 (hereinafter, referred to as "region$_{T24-P474}$"). In the region$_{T24-P474}$, a region corresponding to a serine residue at position 60 to a glutamine residue at position 84 (hereinafter, also referred to as "region$_{S60-Q84}$"), a region corresponding to an asparagine residue at position 95 to a cysteine residue at position 157 (hereinafter, also referred to as "region$_{N95-C157}$"), a region corresponding to a glutamine residue at position 190 to an asparagine residue at position 194 (hereinafter, also referred to as "region$_{Q190-N194}$"), a region corresponding to a leucine residue at position 220 to a glutamate residue at position 233 (hereinafter, also referred to as "region$_{L220-E233}$"), a region corresponding to a lysine residue at position 257 to a glutamate residue at position 275 (hereinafter, also referred to as "region$_{K257-E275}$"), a region corresponding to a leucine residue at position 280 to a threonine residue at position 287 (hereinafter, also referred to as "region$_{L280-T287}$"), a region corresponding to an arginine residue at position 301 to a leucine residue at position 333 (hereinafter, also referred to as "region$_{R301-L333}$"), a region corresponding to an alanine residue at position 354 to a lysine residue at position 373 (hereinafter, also referred to as "region$_{A354-K373}$"), a region corresponding to a tyrosine residue at position 394 to an alanine residue at position 436 (hereinafter, also referred to as "region$_{Y394-A436}$") and a region corresponding to a serine residue at position 453 to an alanine residue at position 462 (hereinafter, also referred to as "region$_{S453-A462}$") in SEQ ID NO.: 2 are preferable, from the viewpoint of ensuring high thermal stability and sufficient specific activity.

The mutant reverse transcriptase of the present invention may have a conservative substitution in the region$_{T24-P474}$ in an amino acid sequence corresponding to SEQ ID NO.: 2, within a range which would not hinder the object of the present invention. The conservative substitution includes, for example, a substitution of a specific amino acid residue with an amino acid residue exhibiting similar functions to the specific amino acid residue, the functions including, for example, hydrophobicity, charge, pKa, conformational characteristics and the like. More specifically, the conservative substitution includes, for example, a substitution of one amino acid residue belonging to any one of the following groups I to VI with another amino acid residue belonging to the same group thereto, and the like.

Group I: a glycine residue and an alanine residue
Group II: a valine residue, an isoleucine residue and a leucine residue
Group III: an aspartate residue, a glutamate residue, an asparagine residue and a glutamine residue
Group IV: a serine residue and a threonine residue
Group V: a lysine residue and an arginine residue
Group VI: a phenylalanine residue and a tyrosine residue In addition, within a range which would not hinder the object of the present invention, the mutant reverse transcriptase of the present invention may be an enzyme having any one of amino acid sequences:
(A) an amino acid sequence further including substitution, deletion, insertion or addition of one or several amino acid residues within an amino acid sequence corresponding to SEQ ID NO.: 2 except for a region corresponding to a threonine residue at position 24 to a proline residue at position 474 of SEQ ID NO.: 2, and
(B) an amino acid sequence having at least 80% sequence identity, the sequence identity being obtained by aligning the amino acid sequence with a sequence except for a region corresponding to a threonine residue at position 24 to a proline residue at position 474 in SEQ ID NO.: 2, with the use of BLAST algorithm under conditions of Gap Costs (Existence 11 and Extension 1), Expect 10 and Word Size 3,
wherein the mutant reverse transcriptase exhibits a reverse transcriptase activity.

The phrase "substitution, deletion, insertion or addition of one or several of amino acid residue" means substitution, deletion, insertion or addition of a certain number of amino acid residue, the number being within the range that a polypeptide exhibiting a reverse transcriptase activity is obtained. Particularly, "one or several" refers to 1 to 30, preferably 1 to 20, further preferably 1 to 10, and more preferably 1 to 3.

The sequence identity is 80% or more, preferably 90% or more, further preferably 95% or more, and particularly preferably 100%, as the value obtained by alignment and calculation with the use of BLAST algorithm under the conditions of Gap Costs (Existence 11, Extension 1), Expect 10, Word Size 3, from the viewpoint of ensuring high thermal stability and sufficient specific activity.

In the mutant reverse transcriptase, it is preferred that at least one of negatively-charged amino acid residues in amino acid residues localized in the region$_{T24\text{-}P474}$ is substituted with the positively-charged amino acid residue or the nonpolar amino acid residue, from the viewpoint of ensuring high thermal stability.

The negatively-charged amino acid residue includes, for instance, an aspartate residue and a glutamate residue. The negatively-charged amino acid residue may be a residue existed in a position affecting shape change, as long as the polypeptide in which the negatively-charged amino acid residue in the amino acid sequence of the WTRT is substituted with the positively-charged amino acid residue or the nonpolar amino acid residue can exhibit the reverse transcriptase activity.

The mutant reverse transcriptase of the present invention is preferably a mutant reverse transcriptase in which at least an amino acid residue corresponding to a glutamate residue at position 286 of SEQ ID NO.: 2, as the negatively-charged amino acid residue, in an amino acid sequence corresponding to SEQ ID NO.: 2 is substituted with the positively-charged amino acid residue or the nonpolar amino acid residue, the mutant reverse transcriptase exhibiting a reverse transcriptase activity, from the viewpoint of ensuring high thermal stability and ensuring sufficient specific activity.

In addition, in the mutant reverse transcriptase of the present invention, a negatively-charged amino acid residue in amino acid residues localized in the region$_{T24\text{-}P474}$, the amino acid residues being residues except for an amino acid residue corresponding to a glutamate residue at position 286 and/or another amino acid residue, can be substituted with the positively-charged amino acid residue or the nonpolar amino acid residue, within a range which would not hinder the object of the present invention. In particular, the mutant reverse transcriptase of the present invention is an enzyme in which residues corresponding to at least one of amino acid residues in an amino acid sequence corresponding to SEQ ID NO.: 2:

a glutamate residue at position 69,
an aspartate residue at position 108,
a glutamate residue at position 117,
an aspartate residue at position 124,
a glutamate residue at position 286,
a glutamate residue at position 302,
a tryptophan residue at position 313,
a leucine residue at position 435, and
an asparagine residue at position 454, are substituted with positively-charged amino acid residues or nonpolar amino acid residues, wherein the enzyme exhibits a reverse transcriptase activity. In this case, although a substitution of a glutamate residue at position 302 with arginine can improve more thermal stability than that of WTRT, the substitution of a glutamate residue at position 302 with arginine is excluded, from the viewpoint of ensuring higher thermal stability.

From the viewpoint of ensuring higher thermal stability, the mutant reverse transcriptase of the present invention is preferably an enzyme containing an amino acid sequence having at least one substitution selected from the group consisting of the following amino acid residue substitutions (a) to (i):

(a) a substitution of a residue corresponding to a glutamate residue at position 286 in SEQ ID NO.: 2 with an alanine residue, a lysine residue or an arginine residue, (b) a substitution of a residue corresponding to a glutamate residue at position 302 in SEQ ID NO.: 2 with an alanine residue or a lysine residue, (c) a substitution of a residue corresponding to a leucine residue at position 435 in SEQ ID NO.: 2 with an alanine residue, a lysine residue or an arginine residue, (d) a substitution of a residue corresponding to an aspartate residue at position 124 in SEQ ID NO.: 2 with an alanine residue, a lysine residue or an arginine residue, (e) a substitution of a residue corresponding to a glutamate residue at position 69 in SEQ ID NO.: 2 with an alanine residue or an arginine residue, (f) a substitution of a residue corresponding to an aspartate residue at position 108 in SEQ ID NO.: 2 with an alanine residue, a lysine residue or an arginine residue, (g) a substitution of a residue corresponding to a glutamate residue at position 117 in SEQ ID NO.: 2 with an alanine residue or a lysine residue, (h) a substitution of a residue corresponding to a tryptophan residue at position 313 in SEQ ID NO.: 2 with an alanine residue, a lysine residue or an arginine residue, and (i) a substitution of a residue corresponding to an asparagine residue at position 454 in SEQ ID NO.: 2 with an alanine residue or an arginine residue, in amino acid sequence corresponding to SEQ ID NO.: 2, wherein the enzyme exhibits a reverse transcriptase activity.

When the mutant reverse transcriptase of the present invention has one mutation selected from the above amino acid residue substitutions (a) to (i) (namely, the mutant reverse transcriptase is a single mutant), from the viewpoint of ensuring higher thermal stability, the mutant reverse transcriptase of the present invention preferably contains amino acid sequence having any one of substitutions:

(a-1) a substitution of a residue corresponding to a glutamate residue at position 286 in SEQ ID NO.: 2 with an alanine residue, (b-1) a substitution of a residue corresponding to a glutamate residue at position 302 in SEQ ID NO.: 2 with a lysine residue, (c-1) a substitution of a residue corresponding to a leucine residue at position 435 in SEQ ID NO.: 2 with an arginine residue, and (d-1) a substitution of a residue corresponding to an aspartate residue at position 124 in SEQ ID NO.: 2 with an arginine residue, in an amino acid sequence corresponding to SEQ ID NO.: 2, wherein the mutant reverse transcriptase exhibits a reverse transcriptase activity.

When the mutant reverse transcriptase of the present invention has several types of mutations selected from amino acid residue substitutions (a) to (i) (namely the mutant reverse transcriptase is a multiple mutant), from the viewpoint of ensuring higher thermal stability, the mutant reverse transcriptase preferably contains the following amino acid sequence:

(I) an amino acid sequence having the following amino acid residue substitutions (a-1) to (c-1):

(a-1) a substitution of a residue corresponding to a glutamate residue at position 286 in SEQ ID NO.: 2 with an alanine residue, (b-1) a substitution of a residue corresponding to a glutamate residue at position 302 in SEQ ID NO.: 2 with a lysine residue, and (c-1) a substitution of a residue corresponding to a leucine residue at position 435 in SEQ ID NO.: 2 with an arginine residue in an amino acid sequence corresponding to SEQ ID NO.: 2, or
(II) an amino acid sequence further including the following substitution:
- (d-1) a substitution of a residue corresponding to an aspartate residue at position 124 in SEQ ID NO.: 2 with an arginine residue in the above amino acid sequence (I), and exhibits a reverse transcriptase activity.

When a reverse transcriptase having no RNase H activities is required as the reverse transcriptase, the mutant reverse transcriptase of the present invention can be a mutant reverse transcriptase containing an amino acid sequence further including the following substitution:
- (e-1) a substitution of a residue corresponding to an aspartate residue at position 524 in SEQ ID NO.: 2 with an alanine residue, in the amino acid sequence (I) or (II),
wherein the mutant reverse transcriptase exhibits a reverse transcriptase activity.

2. Nucleic Acid Encoding Mutant Reverse Transcriptase

The nucleic acid of the present invention is a nucleic acid encoding the mutant reverse transcriptase of the present invention. Since the nucleic acid of the present invention encodes the mutant reverse transcriptase, the mutant reverse transcriptase can be easily obtained by expressing the mutant reverse transcriptase encoded the nucleic acid.

The nucleic acid includes, for instance, DNA, mRNA, and the like, but the present invention is not limited to those exemplified ones.

The nucleic acid of the present invention can be obtained by, for instance, introducing site-directed mutation into a nucleic acid encoding WTRT so that an amino acid residue in the DNA interaction region of the WTRT is substituted with a positively-charged amino acid residue or a nonpolar amino acid residue.

The introduction of site-directed mutation into a nucleic acid can be carried out by, for instance, PCR using primers designed so as to substitute an amino acid residue in the DNA interaction region of the WTRT with a positively-charged amino acid residue or a nonpolar amino acid residue, and the like.

3. Method for Producing Mutant Reverse Transcriptase

The mutant reverse transcriptase of the present invention can be obtained by using the nucleic acid of the present invention, to express the mutant reverse transcriptase encoded thereby. The present invention encompasses the method for producing the mutant reverse transcriptase.

The production method of the present invention is a method for producing the above-mentioned mutant reverse transcriptase, including the steps of:
- (i) culturing a cell harboring the nucleic acid of the present invention to express the mutant reverse transcriptase encoded by the nucleic acid, thereby giving a culture, and
- (ii) collecting the mutant reverse transcriptase from the culture obtained in the above step.

First, a culture is obtained by culturing a cell harboring the nucleic acid of the present invention to express the mutant reverse transcriptase encoded by the nucleic acid {"step (i)"}.

The cell harboring the nucleic acid can be obtained by, for instance, transforming a host cell with the use of a carrier for gene transfer, and the like.

The host cell includes, for instance, a cell of bacterium including *Escherichia coli* and the like; an insect cell; an Yeast cell; a plant cell; an animal cell, and the like, but the present invention is not limited to those exemplified ones. Among them, from the viewpoint of purifying easily the mutant reverse transcriptase and producing the mutant reverse transcriptase in large quantities, the cell is preferably the cell of the bacterium, more preferably the cell of *Escherichia coli*. The cell of *Escherichia coli* includes, for instance, BL21 (DE3), and the like, but the present invention is not limited to those exemplified ones.

The carrier for gene transfer can be a biological carrier or a nonbiological carrier. The biological carrier includes, for instance, a plasmid vector, a phage vector, a viral vector, and the like, but the present invention is not limited to those exemplified ones. In addition, the nonbiological carrier includes, for instance, a gold particle, a dextran, a liposome, and the like, but the present invention is not limited to those exemplified ones. The carrier for gene transfer can be appropriately selected depending on the host cell used. For instance, when the host cell is *Escherichia coli*, the plasmid vector or phage vector can be used as the carrier for gene transfer. When the host cell is *Escherichia coli* BL21(DE3), pET plasmid vectors can be used. In this case, the mutant reverse transcriptase can be overexpressed and the mutant reverse transcriptase can be easily purified.

The vector may contain an element for facilitating purification of the mutant reverse transcriptase, for instance, an extracellular secreting signal, a His tag, and the like.

When the carrier for gene transfer is the plasmid vector, the phage vector or the viral vector, which is the biological carrier, the carrier for gene transfer can be prepared by inserting the nucleic acid into a cloning site of the plasmid vector, the phage vector or the viral vector, thereby operably linking the nucleic acid to the plasmid vector, the phage vector or the viral vector under the control of a promoter. Here, in the present specification, "operably linking" means linking in such a way as to express a polypeptide encoded by the nucleic acid in a biologically active state under the control of an element such as a promoter.

On the other hand, when the carrier for gene transfer is the nonbiological carrier, the carrier for gene transfer can be prepared by fixing a nucleic acid construct to the nonbiological carrier, the nucleic acid construct being obtained by linking the nucleic acid under the control of a promoter as the occasion demands. The nucleic acid construct can contains an element necessary for gene expression including a replication origin, a terminator, or the like.

Transformation can be carried out by a transformation method depending on the type of the carrier for gene transfer used. The transformation method includes, for instance, an electroporation method, a calcium phosphate method, a DEAE-dextran method, a particle gun method, and the like, but the present invention is not limited to those exemplified ones.

In the above step (i), culture conditions of the cell harboring the nucleic acid can be set depending on the type of the host cell used, and the like. When the nucleic acid is operably linked thereto under the control of an inducible promoter, the cell harboring the nucleic acid can be cultured under the expression inducible conditions depending on the type of the promoter.

Next, the mutant reverse transcriptase is collected from the culture obtained in the above step (i) {"step (ii)"}.

When the mutant reverse transcriptase is accumulate in the cell, the mutant reverse transcriptase can be isolated from cells which is collected by subjecting a culture to centrifugation in the above step (ii). In this case, the mutant reverse transcriptase can be isolated by, for example, disrupting the cell with ultrasonic homogenization method, bacteriolysis method, freeze-fracture method and the like, and subjecting the resulting cell extract to centrifugation, ultra centrifugation, ultrafiltration, salting-out, dialysis, ion-exchange column chromatography, adsorption column chromatography, affinity chromatography, gel filtration column chromatography and the like.

Alternatively, when the mutant reverse transcriptase is extracellularly secreted, the mutant reverse transcriptase can be isolated from the supernatant of culture which is obtained by subjecting culture to centrifugation, filtration or the like, thereby collecting the supernatant of culture.

4. Reverse Transcription Method

The reverse transcription method of the present invention is characterized in that cDNA is synthesized from RNA, by using the mutant reverse transcriptase of the present invention. The mutant reverse transcriptase of the present invention has high thermal stability as compared to thermal stability of the wild-type reverse transcriptase. Thus, according to the reverse transcription method of the present invention, a reverse transcription can be performed in a wide temperature range including a high temperature sufficient to inhibit the formation of secondary structure of RNA. Therefore, the reverse transcription method of the present invention can efficiently perform a reverse transcription regardless the type of RNA, and is versatile.

In the reverse transcription method of the present invention, a reverse transcription can be performed by incubating the mutant reverse transcriptase, RNA, an oligonucleotide primer complementary to the RNA, and four types of deoxyribonucleoside triphosphates in a buffer for reverse transcription.

Since the reaction temperature in a reverse transcription varies depending on the type of the RNA used, the type of the mutant reverse transcriptase used, and the like, it is preferred to appropriately set the reaction temperature depending on the type of the RNA used, the type of the mutant reverse transcriptase used, and the like. For example, when the RNA used is RNA unlikely to form secondary structure at reaction temperature suitable for WT, the reaction temperature can be set to be 37 to 45° C. In addition, for example, when the RNA used is RNA likely to form secondary structure at reaction temperature suitable for WT, the reaction temperature can be set to be a temperature higher than the reaction temperature suitable for WT, for example, 45 to 60° C.

Since the concentration of the reverse transcriptase in a reaction system upon reverse transcription varies depending on the use of the reverse transcription method of the present invention, it is preferred to appropriately set the concentration depending on the use. The concentration of the reverse transcriptase is generally preferably 0.001 to 0.1 µM.

The concentration of the oligonucleotide primer in a reaction system upon reverse transcription is generally preferably 0.1 to 10 µM.

Since the concentration of the four types of deoxyribonucleoside triphosphates in a reaction system upon reverse transcription varies depending on the concentration or length of the RNA targeted and the like, it is preferred to appropriately set the concentration depending on the concentration or length of the RNA targeted and the like. The concentration of the four types of deoxyribonucleoside triphosphates is generally preferably 0.01 to 1 µM.

The buffer for reverse transcription can be appropriately selected depending on the type of the mutant reverse transcriptase used. The buffer for reverse transcription may contain a divalent cation, for example, a magnesium ion, a manganese ion, or the like. In addition, the buffer for reverse transcription may contain a component such as a reducing agent (for example, dithiothreitol, or the like), a stabilizer (for example, glycerol, trehalose, or the like), and an organic solvent (for example, dimethyl sulfoxide, formamide, or the like) as necessary, within a range which would not hinder the object of the present invention.

Since the concentration of the divalent cation in the buffer for reverse transcription varies depending on the type of the reverse transcriptase, other components contained in the buffer for reverse transcription, and the like, it is preferred to appropriately set the concentration depending on the type of the reverse transcriptase, other components contained in the buffer for reverse transcription, and the like. The concentration of the divalent cation is generally 1 to 30 mM.

Since the pH of the buffer for reverse transcription varies depending on the type of the reverse transcriptase, other components contained in the buffer for reverse transcription, and the like, it is preferred to appropriately set the pH depending on the type of the reverse transcriptase, other components contained in the buffer for reverse transcription, and the like. The pH of the buffer for reverse transcription is generally 6.0 to 9.5.

5. Kit for Reverse Transcription

The kit for reverse transcription of the present invention is a kit for performing a reverse transcription and is characterized in that the kit contains the mutant reverse transcriptase of the present invention. Since the kit for reverse transcription of the present invention contains the mutant reverse transcriptase of the present invention having high thermal stability, it is suitable for a reverse transcription in a wide temperature range including a high temperature sufficient to inhibit the formation of secondary structure of RNA. Therefore, the kit for reverse transcription of the present invention can efficiently perform a reverse transcription regardless the type of RNA, and is versatile.

The kit for reverse transcription of the present invention may contain a reagent necessary for performing a reverse transcription, in addition to the mutant reverse transcriptase. The reagent includes, for example, an RNA used as a template of reverse transcription, an oligonucleotide primer complementary to the RNA, four types of deoxyribonucleoside triphosphates, a buffer for reverse transcription, an organic solvent, and the like. The buffer for reverse transcription is the same as the buffer for reverse transcription used in the above reverse transcription method.

In the kit for reverse transcription of the present invention, the mutant reverse transcriptase may be sealed in a container in which a buffer for preservation containing a stabilizer such as glycerol or trehalose is stored. The buffer for preservation includes a buffer having a pH depending of the pH stability of the mutant reverse transcriptase.

In addition, the reagent necessary for performing a reverse transcription may be sealed in a container different from the container in which a mutant reverse transcriptase is stored, and may be sealed in the same container as the mutant reverse transcriptase, as long as the reverse transcription during the storage of the reagent is not progressed. The reagent may be sealed in a container in an amount suitable for performing a reverse transcription. Since a user is no longer necessary to mix each reagent in an amount suitable for reverse transcription, handling is easy.

6. Detection Kit

The detection kit of the present invention is a kit for detecting a marker in a sample containing RNA obtained from the living body, and is characterized in that the kit contains the mutant reverse transcriptase and the reagent for detecting a marker. Since the detection kit of the present invention contains the mutant reverse transcriptase having high thermal stability, the kit is suitable for a reverse transcription in a wide temperature range including a high temperature sufficient to inhibit the formation of secondary structure of RNA. Therefore, the detection kit of the present invention can be used on various samples, and is versatile.

The marker includes a nucleotide sequence specific to a virus or bacteria contained in the living body, an RNA having a nucleotide sequence specific to a disease, and the like. Here, "a nucleotide sequence specific to a virus or bacteria" as used herein refers to a nucleotide sequence present in a virus or bacteria but not present in the living body. In addition, "a nucleotide sequence specific to a disease" refers to a nucleotide sequence present in the living body affected with a disease but not present in the normal living body not affected with a disease.

The virus is not particularly limited, and includes, for example, HPV, HIV, influenza virus, HCV, norovirus, West Nile virus, and the like. In addition, the bacterium includes, for example, *Bacillus cereus, Salmonella*, enterohemorrhagic *E. coli, Vibrio, Campylobacter*, methicillin-resistant *Staphylococcus aureus*, and the like. The disease includes, for example, cancer, diabetes, heart disease, hypertension, infectious diseases, and the like.

The reagent for detecting a marker includes, for example, a probe complementary to RNA which is the marker, to which a fluorescent substance or radioactive substance is conjugated, a fluorescent substance specifically intercalating into a double-stranded nucleic acid (for example, ethidium bromide), and the like.

The detection kit of the present invention may contain, for example, four types of deoxyribonucleoside triphosphates, a buffer for reverse transcription, an organic solvent, an RNA which is a positive standard, RNA which is a negative standard, and the like, in addition to the mutant reverse transcriptase and the reagent for detecting a marker. The buffer for reverse transcription is the same as the buffer for reverse transcription used in the reverse transcription method.

In the detection kit of the present invention, the mutant reverse transcriptase may be sealed in a container in which a buffer for preservation containing a stabilizer such as glycerol or trehalose is stored. The buffer for preservation is the same as the buffer for preservation in the kit for reverse transcription.

In addition, the reagents including the four types of deoxyribonucleoside triphosphates, the buffer for reverse transcription, or the like may be sealed in a container different from the container in which a mutant reverse transcriptase is stored, and may be sealed in the same container as the mutant reverse transcriptase, as long as the reverse transcription during the storage of the reagent is not progressed. The reagent may be sealed in a container in an amount suitable for performing a reverse transcription from the same viewpoint as the kit for reverse transcription.

7. Method for Improving Thermal Stability of Nucleic Acid-Related Enzyme

The method for improving thermal stability of a nucleic acid-related enzyme of the present invention is a method for improving thermal stability of a nucleic acid-related enzyme having a nucleic acid interaction region which interacts with a nucleic acid, including:

introducing a mutation into a nucleotide sequence corresponding to the nucleic acid interaction region in a nucleic acid encoding a wild-type nucleic acid-related enzyme, to form a nucleic acid interaction region having a positive effective charge larger than the nucleic acid interaction region of a wild-type nucleic acid-related enzyme, wherein the mutation is a substitution of an amino acid residue in the nucleic acid interaction region with a positively-charged amino acid residue or a nonpolar amino acid residue.

The nucleic acid-related enzyme has a nucleic acid interaction region interacting with a nucleic acid. Therefore, as well as the mutant reverse transcriptase of the present invention, it is expected that high thermal stability can be ensured by substituting an amino acid residue in a nucleic acid interaction region with a positively-charged amino acid residue or a nonpolar amino acid residue.

The nucleic acid-related enzyme may be an enzyme having a nucleic acid interaction region interacting with a nucleic acid. The nucleic acid-related enzyme includes, for example, a reverse transcriptase, a DNA polymerase, a restriction enzyme, a methylase, an RNA polymerase, a telomerase, and the like. Among them, the reverse transcriptase is preferable since thermal stability can be further improved.

The introduction of the mutation into a nucleotide sequence corresponding to the nucleic acid interaction region in a nucleic acid encoding a wild-type nucleic acid-related enzyme can be performed by PCR using primers designed so as to substitute an amino acid residue in the nucleic acid interaction region of a wild-type nucleic acid-related enzyme with a positively-charged amino acid residue or a nonpolar amino acid residue, or the like.

The position of the amino acid residue to be mutated varies depending on the type of a nucleic acid-related enzyme, and includes, a position of an amino acid residue which is adjacent to a phosphoric acid group of a nucleic acid and does not cause a shape change that inhibits an activity of the nucleic acid-related enzyme in the nucleic acid interaction region of a nucleic acid-related enzyme, a position of an amino acid residue which is adjacent to an amino acid group having a negative charge of a reverse transcriptase and does not cause a shape change that inhibits an activity of the nucleic acid-related enzyme, and the like.

The nucleic acid-related enzyme with improved thermal stability can be produced in the same manner as in the method for producing a mutant reverse transcriptase using a nucleic acid into which a mutation is introduced.

EXAMPLES

Hereinafter, the present invention will be more specifically on the basis of examples, but the present invention is not intended to be restricted by the examples.

Production Example 1

A DNA (SEQ ID NO.:1) encoding a wild-type MMLV reverse transcriptase (hereinafter, also simply referred to as "WT") was inserted into a pET-22b(+) plasmid, to give an expression plasmid pET-MRT.

*Escherichia coli* BL21 (DE3) was transformed using the resulting plasmid. The resulting cell was cultured at 30° C. in L-broth containing 50 μg/mL ampicillin, to give a transformed cell.

Subsequently, the transformed cell was inoculated into 3 mL of L-broth containing 50 μg/mL ampicillin and incubated at 30° C. for 16 hours while shaking. Thereafter, the transformed cell was cultured with an autoinduction system {manufactured by Novagen, trade name: Overnight Express Autoinduction System}, to express a protein.

A bacterial lysis reagent {manufactured by Promega KK., trade name: FastBreak Cell Lysis Reagent} contained in a protein purification system {manufactured by Promega KK., trade name: HisLink Spin Protein Purification System} was added to the resulting culture, to lyse the transformed cell. Subsequently, a protein purification resin {manufactured by Promega KK., trade name: HisLink Spin Protein Purification Resin} contained in the protein purification system was added to the resulting lysate.

Thereafter, the lysate containing the resin was transferred to a column {manufactured by Promega KK., trade name: HisLink Spin Column}. Thereafter, a resin in the column was washed to remove an unbound protein and the like. Subsequently, a protein adsorbed to the column was eluted using 0.2 mL of an eluent buffer {composition: 100 mM HEPES—sodium hydroxide buffer (pH 7.5), and 500 mM imidazole}, thereby collecting a fraction containing WT.

By SDS-PAGE, the resulting WT was confirmed to show a single band of 75 kDa.

The magnitude of effective charge of a DNA interaction region of WT is +7 when calculated according to the formula (I) defining each charge score of a lysine residue and an arginine residue which are positively-charged amino acid residues as "+1" and each charge score of an aspartate residue and a glutamate residue which are negatively-charged amino acid residues as "−1".

Production Example 2

(1) Design of Mutation

In order to substitute a negatively-charged amino acid residue in a region related to the interaction with a template primer in WT (a region corresponding to a threonine residue at position 24 to a proline residue at position 474 in the amino acid sequence shown in SEQ ID NO.: 2) for a positively-charged amino acid residue (a lysine residue or an arginine residue) or a nonpolar amino acid residue (an alanine residue), a primer for a site-directed mutation was designed.

As an amino acid residue to be substituted (a negatively-charged amino acid residue), 7 residues (Glu69, Gln84, Asp108, Asp114, Glu117, Glu123, and Asp124) located in a fingers domain of the region, 3 residues (Glu286, Glu302, and Trp313) located in a thumb domain, and 2 residues (Leu435 and Asn454) located in a connection domain were selected. The localization position of amino acid residues to be substituted selected in Production Example 2 in the wild-type MMLV reverse transcriptase is shown in FIG. 1.

The primer for site-directed mutation is a primer designed so as to generate a substitution of the amino acid residue shown in Table 1.

TABLE 1

| Experimental Number | | |
|---|---|---|
| 1 | E69A | Substitution of E at position 69 with A |
| 2 | E69K | Substitution of E at position 69 with K |
| 3 | E69R | Substitution of E at position 69 with R |
| 4 | Q84A | Substitution of Q at position 84 with A |
| 5 | Q84K | Substitution of Q at position 84 with K |
| 6 | Q84R | Substitution of Q at position 84 with R |
| 7 | D108A | Substitution of D at position 108 with A |
| 8 | D108K | Substitution of D at position 108 with K |
| 9 | D108R | Substitution of D at position 108 with R |
| 10 | D114A | Substitution of D at position 114 with A |
| 11 | D114K | Substitution of D at position 114 with K |
| 12 | D114R | Substitution of D at position 114 with R |
| 13 | E117A | Substitution of E at position 117 with A |
| 14 | E117K | Substitution of E at position 117 with K |
| 15 | E117R | Substitution of E at position 117 with R |
| 16 | E123A | Substitution of E at position 123 with A |
| 17 | E123K | Substitution of E at position 123 with K |
| 18 | E123R | Substitution of E at position 123 with R |
| 19 | D124A | Substitution of D at position 124 with A |
| 20 | D124K | Substitution of D at position 124 with K |
| 21 | D124R | Substitution of D at position 124 with R |

TABLE 1-continued

| Experimental Number | | |
|---|---|---|
| 22 | E286A | Substitution of E at position 286 with A |
| 23 | E286K | Substitution of E at position 286 with K |
| 24 | E286R | Substitution of E at position 286 with R |
| 25 | E302A | Substitution of E at position 302 with A |
| 26 | E302K | Substitution of E at position 302 with K |
| 27 | E302R | Substitution of E at position 302 with R |
| 28 | W313A | Substitution of W at position 313 with A |
| 29 | W313K | Substitution of W at position 313 with K |
| 30 | W313R | Substitution of W at position 313 with R |
| 31 | L435A | Substitution of L at position 435 with A |
| 32 | L435K | Substitution of L at position 435 with K |
| 33 | L435R | Substitution of L at position 435 with R |
| 34 | N454A | Substitution of N at position 454 with A |
| 35 | N454K | Substitution of N at position 454 with K |
| 36 | N454R | Substitution of N at position 454 with R |

(2) Preparation of Single Mutant of MMLV Reverse Transcriptase

Using the pET-MRT, primers for site-directed mutation, and a kit for site-directed mutation {manufactured by Stratagene Corporation, trade name: Quikchange™ site-directed mutagenesis kit}, a site-directed mutation was introduced into a DNA encoding WT on the pET-MRT. Here, whether or not a mutation was introduced into a DNA contained in the resulting plasmid for expressing a mutant was confirmed by a DNA sequencer {manufactured by Shimadzu Corporation, trade name: DSQ-2000}.

Next, the same procedures as in Production Example 1 were carried out except that the plasmid for expressing a mutant was used in place of the pET-MRT in Production Example 1, to give single mutants of Experimental Numbers: 1 to 36. As the result of SDS-PAGE analysis, all resulting single mutants were confirmed to show a single band of 75 kDa.

Test Example 1

In a solution for incubation {composition: 10 mM potassium phosphate buffer (pH 7.6), 2 mM dithiothreitol, 0.2% by volume Triton™ X-100, and 10% by volume glycerol}, WT obtained in Production Example 1 (100 nM) or a single mutant obtained in Production Example 2 (100 nM) was incubated at 50° C. for 15 minutes in the presence or absence of 28 μM poly(rA)·p(dT)$_{15}$, to carry out heat treatment. Thereafter, the WT or the single mutant was incubated on ice for 30 to 60 minutes.

Subsequently, in a reaction solution {composition: 25 mM Tris hydrochloride buffer (pH 8.3), 50 mM potassium chloride, 2 mM dithiothreitol, 5 mM magnesium chloride, 12.5 μM poly(rA)·p(dT)$_{15}${concentration converted to p(dt)$_{15}$}, and 0.2 mM [methyl-$^3$H]dTTP (1.85 Bq/pmol) {manufactured by GE Healthcare}}, 10 nM WT or single mutant was incubated at 37° C.

A twenty microliters of the product after incubation for a certain period of time (2.5, 5.0, or 7.5 minute) was collected, and immediately spotted on a glass filter {manufactured by Whatman Ltd., trade name: GF/C, a diameter of 2.5 cm}. Subsequently, the glass filter was washed with a cooled 5% by mass trichloroacetic acid aqueous solution for 10 minutes. Thereafter, the glass filter was washed with a cooled 95% by mass ethanol aqueous solution. Thereby, the [$^3$H]dTTP unincorporated into poly(rA)·p(dT)$_{15}$ was removed. The washing with a trichloroacetic acid aqueous solution was repeated three times. Also, the washing with an ethanol aqueous solution was repeated once.

Thereafter, the glass filter was dried. The glass filter was put in 2.5 mL of a reagent for liquid scintillation {manufactured by National Diagnostics, trade name: Ecoscint H}, and thereafter radioactivity was counted. Based on the radioactivity, the amount of [$^3$H]dTTP incorporated into poly(rA)·p(dT)$_{15}$ (referred to as "amount of dTTP incorporated") was calculated.

Based on the time-dependent change of the amount of dTTP incorporated, the initial reaction rate was calculated. Subsequently, from the initial reaction rate in the case where heat treatment was not performed (referred to as "initial reaction rate A") and the initial reaction rate in the case where heat treatment was performed (referred to as "initial reaction rate B"), a remaining activity was calculated. Using the formula (II):

Remaining Activity (%)=(Initial Reaction Rate B/Initial Reaction Rate A)×100     (II), the remaining activity was calculated.

Based on the calibration curve generated according to Bradford method using a known amount of the preparation of bovine serum albumin and a protein assay reagent {manufactured by NACALAI TESQUE, INC., trade name: Protein Assay CBB Solution}, the amounts of WT and each single mutant of Experimental Numbers: 1 to 36 were examined. Subsequently, a reverse transcription activity was determined, based on the amounts of dTTP incorporated of WT and each single mutant of Experimental Numbers: 1 to 36 in the case where heat treatment was not performed. Here, 1 unit in the reverse transcription activity was defined as the amount of reverse transcriptase incorporating 1 nmol of dTTP into poly(rA)·p(dT)$_{15}$ for 10 minutes. Thereafter, based on each reverse transcription activity of WT and Experimental Numbers: 1 to 36 and the amounts of WT and each single mutant of Experimental Numbers: 1 to 36, specific activity was calculated.

Figure 2:
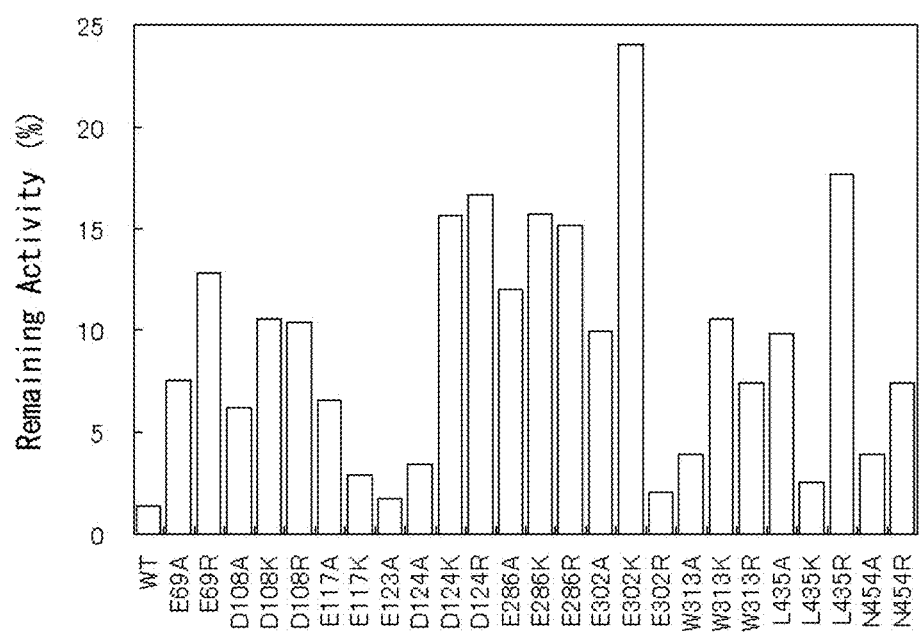
FIG. 2 is a graph showing the result of examining the relationship between the type of an amino acid residue substitution and a remaining activity in Test Example 1.

Based on the remaining activity and specific activity of WT and each single mutant of Experimental Numbers: 1 to 36, whether or not an amino acid residue to be substituted was a residue causing thermal stability higher than WT by introducing a site-directed mutation was evaluated. The evaluation criteria are shown in Table 2, and the evaluation result is shown in Table 3. In addition, the result of examining the relationship between the type of amino acid residue substitution and a remaining activity in Test Example 1 is shown in FIG. 2. In FIG. 2, the remaining activities of the representative example of WT and single mutants are shown.

TABLE 2

| Evaluation | Evaluation Criteria |
|---|---|
| AA | All three types of mutants having the same amino acid residue to be substituted show thermal stability higher than the wild-type MMLV reverse transcriptase. |
| A | Two out of three types of mutants having the same amino acid residue to be substituted show thermal stability higher than the wild-type MMLV reverse transcriptase. |
| B | One out of three types of mutants having the same amino acid residue to be substituted shows thermal stability higher than the wild-type MMLV reverse transcriptase. |
| C | The specific activity or remaining activity of one out of three types of mutants having the same amino acid residue to be substituted is 0. |

TABLE 3

| Amino Acid Residue to Be Substituted | Evaluation |
|---|---|
| E69 | A |
| Q84 | C |
| D108 | AA |
| D114 | C |
| E117 | A |
| E123 | B |
| D124 | AA |
| E286 | AA |
| E302 | AA |
| W313 | AA |
| L435 | AA |
| N454 | A |

It can be seen from the result shown in Table 3 that the remaining activity of the single mutant into which a site-directed mutation was introduced at E69, D108, E117, D124, E286, E302, W313, L435, or N454 in the amino acid residues to be subjected, is higher than the remaining activity of WT. Therefore, it can be seen that thermal stability can be improved as compared to WT by substituting an amino acid residue corresponding to E69, D108, E117, D124, E286, E302, W313, L435, or N454 with a positively-charged amino acid residue or a nonpolar amino acid residue, in the amino acid sequence shown in SEQ ID NO.: 2.

Further, it can be seen from the result shown in Table 2 that the remaining activity of each of two single mutants among three types of single mutants into which a site-directed mutation was introduced at E286 surpasses 15%. In addition, it can be seen that the remaining activity of each of two single mutants among three types of single mutants into which a site-directed mutation was introduced at D124 surpasses 15%.

It can be seen from these results that introduction of a mutation substituting an amino acid residue with a positively-charged amino acid residue or a nonpolar amino acid residue into the region related to the interaction with a template primer in WT (the region corresponding to a threonine residue at position 24 to a proline residue at position 474 in the amino acid sequence shown in SEQ ID NO.: 2) has high probability of ensuring high thermal stability.

Example 1

From the amino acid residues to be substituted evaluated in Test Example 1, the amino acid residues to be substituted which were evaluated as AA were selected. Subsequently, from the mutants with the selected amino acid residues substituted with other amino acid residues, four types of mutants (E302K, L435R, D124R, and E286R) were selected, in order of high remaining activity.

The same procedures as in Production Example 2 were carried out except that primers designed so as to generate the substitution of the selected four types of amino acid residues were used in place of primers designed so as to generate the amino acid residue substitution shown in Table 1 in Production Example 2, to give a multiple mutant of MMLV reverse transcriptase (D124R/E286R/E302K/L435R). As the result of SDS-PAGE, the resulting multiple mutant was confirmed to show a single band of 75 kDa.

The score of magnitude of effective charge in a DNA interaction region of the multiple mutant was calculated using the formula (I), based on each number of a lysine residue, an arginine residue, an aspartate residue, and a glutamate residue in the DNA interaction region, defining each charge score of a lysine residue and an arginine residue that are positively-charged amino acid residues as "+1" and each charge score of an aspartate residue and a glutamate residue that are a negatively-charged amino acid residues as "−1". As a result, the score of magnitude of effective charge in the DNA interaction region of the resulting multiple mutant was +13.

Example 2

The same procedures as in Example 1 were carried out except that primers designed so as to generate the substitution of the four types of amino acid residues selected in Example 1 and the substitution of Asp at position 524 with Ala (D524A) in SEQ ID NO.: 2 were used in place of the primers designed so as to generate the substitution of the selected four types of amino acid residues in Example 1, to give a multiple mutant of MMLV reverse transcriptase (D124R/E286R/E302K/L435R/D524A). Here, Asp at position 524 in SEQ ID NO.: 2 is located at the active site of RNase H reaction of WT and is an amino acid residue essential for a catalytic activity. As the result of SDS-PAGE analysis, the resulting multiple mutant was confirmed to show a single band of 75 kDa.

The score of magnitude of effective charge in the DNA interaction region of the resulting multiple mutant was +13.

Example 3

From the substitution of the four types of amino acid residues selected in Example 1, three types of amino acid residue substitutions including E302K, L435R, and E286R were selected. Subsequently, the same procedures as in Example 1 were carried out except that primers designed so as to generate the three types of amino acid residue substitutions were used in place of the primers designed so as to generate the substitutions of the selected four types of amino acid residues in Example 1, to give a multiple mutant of MMLV reverse transcriptase (E286R/E302K/L435R). As the result of SDS-PAGE analysis, the resulting multiple mutant was confirmed to show a single band of 75 kDa.

The score of magnitude of effective charge in the DNA interaction region of the resulting multiple mutant was +11.

Example 4

The same procedures as in Example 1 were carried out except that primers designed so as to generate the substitutions of the three types of amino acid residues selected in Example 3 and D524A were used in place of the primer designed so as to generate the substitution of the selected four types of amino acid residues in Example 1, to give a multiple mutant of MMLV reverse transcriptase (E286R/E302K/L435R/D524A). As the result of SDS-PAGE analysis, the resulting multiple mutant was confirmed to show a single band of 75 kDa.

The score of magnitude of effective charge in the DNA interaction region of the resulting multiple mutant was +11.

Test Example 2

Figure 3:
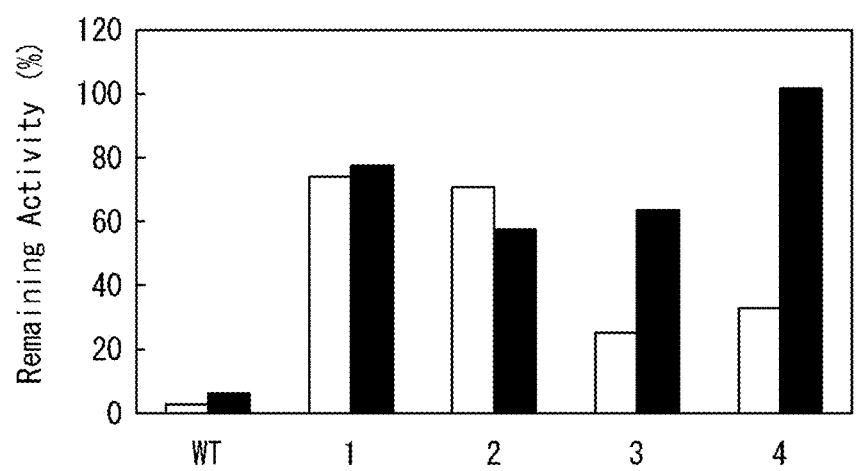
FIG. 3 is a graph showing the result of examining the relationship between the type of multiple mutant and a remaining activity in Test Example 2.

The same procedures as in Test Example 1 were carried out except for using the multiple mutants obtained in Examples 1 to 4, in place of the single mutant obtained in Production Example 2 in Test Example 1, to calculate a remaining activity. The result of examining the relationship between the type of multiple mutant and a remaining activity in Test Example 2 is shown in FIG. 3. In the figure, 1 shows a remaining activity of the multiple mutant obtained in Example 1, 2 shows a remaining activity of the multiple mutant obtained in Example 2, 3 shows a remaining activity of the multiple mutant obtained in Example 3, and 4 shows a remaining activity of the multiple mutant obtained in Example 4. In addition, in the figure, a white bar shows a remaining activity of the multiple mutant in the absence of a template primer, and a black bar shows a remaining activity of the multiple mutant in the presence of a template primer.

It can be seen from the result shown in FIG. 3 that the multiple mutants obtained in Examples 1 to 4 have a remarkably high thermal stability as compared to WT. Therefore, it can be seen that high thermal stability can be ensured by substituting at least E286 with a positively-charged amino acid residue or a nonpolar amino acid residue in the region related to the interaction with a template primer in WT (the region corresponding to a threonine residue at position 24 to a proline residue at position 474 in the amino acid sequence shown in SEQ ID NO.: 2).

In addition, the score of magnitude of effective charge of the region of the multiple mutants obtained in each of Examples 1 to 4 was +11 to +13, and is larger than the score of magnitude of effective charge of the region of WT (+7). Therefore, it can be seen from these results that high thermal stability can be ensured by substituting the amino acid residue in the DNA interaction region with a positively-charged amino acid residue or a nonpolar amino acid residue to locate the positively-charged amino acid residue or the nonpolar amino acid residue in the DNA interaction region, such that the score of magnitude of effective charge of the DNA interaction region is larger than the effective charge in the DNA interaction region of WT.

Test Example 3

In a reaction solution {composition: 25 mM Tris hydrochloride buffer (pH 8.3), 50 mM potassium chloride, 2 mM dithiothreitol, 5 mM magnesium chloride, poly(rA)·p(dT)$_{15}$ at a concentration in the range of 0 to 25 µM {concentration converted to p(dT)$_{15}$}, 0.2 mM [methyl-$^3$H]dTTP (1.85 Bq/pmol) {manufactured by GE Healthcare}}, the multiple mutant obtained in Example 3, the multiple mutant obtained in Example 4 or WT (Comparative Example 1) (5 nM) was incubated at 37° C.

A twenty microliters of the product after incubation for a certain period of time (2.5, 5.0, or 7.5 minutes) was collected, and immediately spotted on a glass filter {manufactured by Whatman Ltd., trade name: GF/C, a diameter of 2.5 cm}. Subsequently, the glass filter was washed with a cooled 5% by mass trichloroacetic acid aqueous solution for 10 minutes. Thereafter, the glass filter was washed with a cooled 95% by mass ethanol aqueous solution. Thereby, the [$^3$H]dTTP unincorporated into poly(rA)·p(dT)$_{15}$ was removed. The washing with a trichloroacetic acid aqueous solution was repeated three times. Also, the washing with an ethanol aqueous solution was repeated once.

Thereafter, the glass filter was dried. The glass filter was put in 2.5 mL of a reagent for liquid scintillation {manufactured by National Diagnostics, trade name: Ecoscint H}, and radioactivity was counted. Based on the radioactivity, the amount of dTTP incorporated was calculated. Based on the time-dependent change of the amount of dTTP incorporated, the initial reaction rate was calculated.

Subsequently, using a substrate [poly(rA)·p(dT)$_{15}$] concentration, an initial reaction rate, and a graph making software {manufactured by Synergy Software, trade name: Kaleida Graph Version 3.5}, based on the Michaelis-Menten rate equation according to the non-linear least-squares regression method, $k_{cat}$ value, $K_m$ value, and $k_{cat}/K_m$ value were calculated. The $k_{cat}$ value, the $K_m$ value, and the $k_{cat}/K_m$ value of each of the multiple mutant obtained in Example 3, the multiple mutant obtained in Example 4 and WT (Comparative Example 1) are shown in Table 4.

TABLE 4

| | | $K_m$(μM) | $k_{cat}$(s$^{-1}$) | $k_{cat}/K_m$(μM$^{-1}$s$^{-1}$) |
|---|---|---|---|---|
| Example 3 | E286R/E302K/L435R | 2.2 ± 1.1 (0.3)*[1] | 5.6 ± 0.6 (0.4)*[1] | 2.5 ± 1.1 (1.7)*[1] |
| Example 4 | E286R/E302K/L435R/D524A | 3.3 ± 0.7 (0.4)*[1] | 6.6 ± 0.4 (0.5)*[1] | 2.0 ± 0.3 (1.3)*[1] |
| Comparative Example 1 | Wild-Type | 8.4 ± 2.0 (1.0)*[1] | 13.0 ± 1.2 (1.0)*[1] | 1.5 ± 0.2 (1.0)*[1] |

*[1] shows a relative value based on the value of Comparative Example 1.

It can be seen from the result shown in Table 4 that the $K_m$ values of the multiple mutant obtained in Example 3 and the multiple mutant obtained in Example 4 are each 30% and 40% of the $K_m$ value of WT. It is suggested from these results that the affinities of the multiple mutant obtained in Example 3 and the multiple mutant obtained in Example 4 to a template primer are higher than the affinity of WT to a template primer.

On the other hand, it can be seen from the result shown in Table 4 that the $k_{cat}$ values of the multiple mutant obtained in Example 3 and the multiple mutant obtained in Example 4 are 40% and 50% of the $k_{cat}$ value of WT, respectively.

Furthermore, it can be seen from the result shown in Table 4 that the $k_{cat}/K_m$ values of the multiple mutant obtained in Example 3 and the multiple mutant obtained in Example 4 are 170% and 130% of the $k_{cat}/K_m$ value of WT. It is suggested from these results that the catalytic efficiencies of the multiple mutant obtained in Example 3 and the multiple mutant obtained in Example 4 are higher than the catalytic efficiency of WT.

Test Example 4

In a solution for incubation {composition: 10 mM potassium phosphate buffer (pH 7.6), 2 mM dithiothreitol, 0.2% by volume Triton™ X-100, and 10% by volume glycerol}, the multiple mutant obtained in Example 3 or the multiple mutant obtained in Example 4 (100 nM) was incubated at 52 to 58° C. for a certain period of time (1, 2, 5, 10, or 15 minute) in the presence of 28 μM poly(rA)·p(dT)$_{15}$, to carry out heat treatment, and thereafter incubated on ice for 30 to 60 minutes.

On the other hand, in the solution for incubation, WT (Comparative Example 1) was incubated at 48 to 52° C. for a certain period of time (1, 2, 5, 10, or 15 minute) in the presence of 28 μM poly(rA)·p(dT)$_{15}$, to carry out heat treatment, and thereafter incubated on ice for 30 to 60 minutes.

Subsequently, in a reaction solution {composition: 25 mM Tris hydrochloride buffer (pH 8.3), 50 mM potassium chloride, 2 mM dithiothreitol, 5 mM magnesium chloride, 12.5 μM poly(rA)·p(dT)$_{15}$ {concentration converted to p(dT)$_{15}$}, and 0.2 mM [methyl-$^3$H]dTTP (1.85 Bq/pmol) {manufactured by GE Healthcare}}, the multiple mutant obtained in Example 3, the multiple mutant obtained in Example 4 or WT (Comparative Example) (10 nM) was incubated at 37° C.

A twenty microliters of the product after incubation for a certain period of time (2.5, 5.0, or 7.5 minute) was collected, and immediately spotted on a glass filter {manufactured by Whatman Ltd., trade name: GF/C, a diameter of 2.5 cm}. Subsequently, the glass filter was washed with a cooled 5% by mass trichloroacetic acid aqueous solution for 10 minutes. Thereafter, the glass filter was washed with a cooled 95% by mass ethanol aqueous solution. Thereby, the [$^3$H]dTTP unincorporated into poly(rA)·p(dT)$_{15}$ was removed. The washing with a trichloroacetic acid aqueous solution was repeated three times. Also, the washing with an ethanol aqueous solution was repeated once.

Thereafter, the glass filter was dried. The glass filter was put in 2.5 mL of a reagent for liquid scintillation {manufactured by National Diagnostics, trade name: Ecoscint H}, and radioactivity was counted. Based on the radioactivity, the amount of dTTP incorporated was calculated.

Based on the time-dependent change of the amount of dTTP incorporated, the initial reaction rate was calculated. Subsequently, from the initial reaction rate in the case where heat treatment was not performed (referred to as "initial reaction rate a") and the initial reaction rate in the case where heat treatment was performed (referred to as "initial reaction rate b"), a remaining activity was calculated. Using the formula (III):

$$\text{Remaining Activity (\%)} = (\text{Initial Reaction Rate } b/\text{Initial Reaction Rate } a) \times 100 \quad (III),$$

the remaining activity was calculated. Subsequently, a logarithmic value of the remaining activity on the incubation time in heat treatment (heat treatment time) was plotted. Next, based on the formula (IV):

$$\ln[B] = A - k_{obs}t \quad (IV),$$

wherein A shows a constant term, B shows a remaining activity (%), and t shows a heat treatment time, the first-order rate constant for thermal inactivation $k_{obs}$ was determined.

In addition, the logarithmic value of $k_{obs}$ based on the temperature in heat treatment was plotted. Next, based on the formula (V):

$$\ln(k_{obs}) = A - (E_a/R)(1/T) \quad (V),$$

wherein A shows a constant term, R shows a gas constant (=8.314 J/K·mol), and T is the absolute temperature (K), using an Arrhenius plot, the activation energy $E_a$ based on the thermal inactivation was determined. By an Arrhenius plot, $T_{50}$ was presumed as a temperature where the $k_{obs}$ value provides 50% of the remaining activity in 10 minutes.

Figure 4:
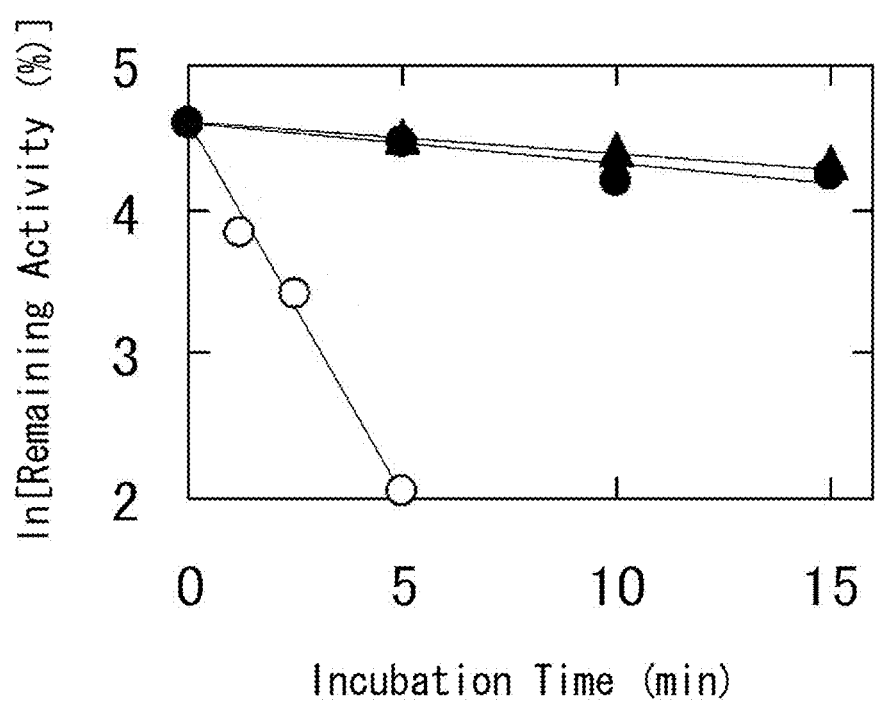
FIG. 4 is a graph showing the result of examining the relationship between incubation time and ln[remaining activity (%)] in Test Example 4.

The result of examining the relationship between incubation time and ln [remaining activity (%)] in Test Example 4 is shown in FIG. 4. FIG. 4 shows the result of performing heat treatment at 52° C. In addition, in the figure, ln [remaining activity (%)] shows a natural logarithmic value of the remaining activity.

Figure 5:
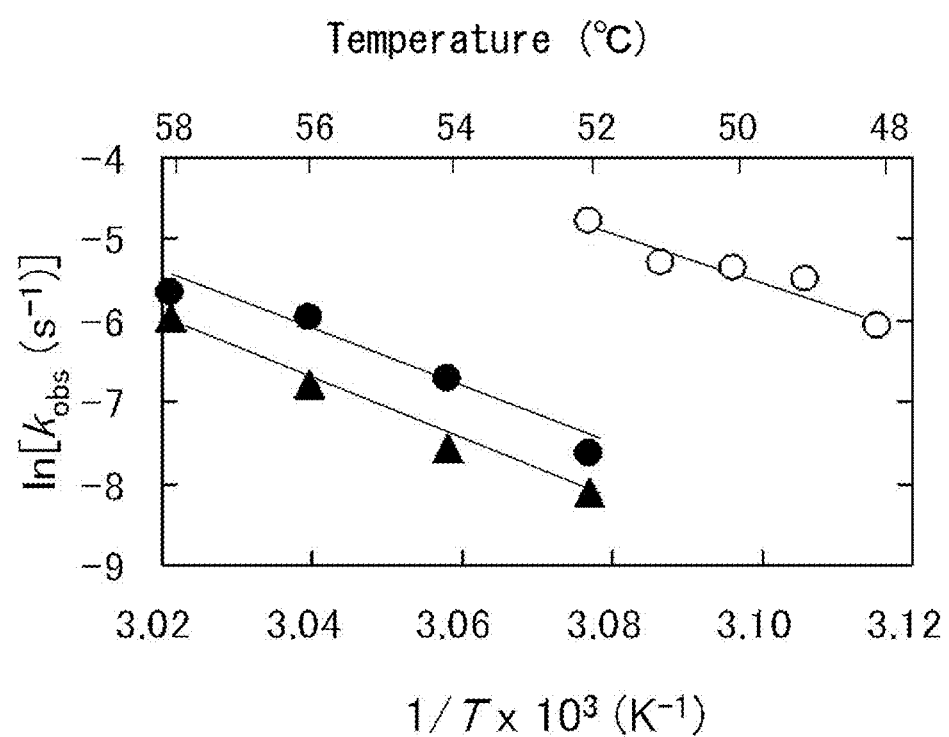
FIG. 5 is a graph showing the result of examining the relationship between temperature and $\ln[k_{obs}(s^{-1})]$ in Test Example 4.

In addition, the result of examining the relationship between temperature and ln [$k_{obs}$(s$^{-1}$)] in Test Example 4 is shown in FIG. 5. In the figure, ln [$k_{obs}$(s$^{-1}$)] shows a natural logarithmic value of $k_{obs}$.

It can be seen from the result shown in FIG. 4 that, while the remaining activity of WT (Comparative Example) decreases to 10% or less by 5 minutes of incubation, the remaining activity of each of the multiple mutant obtained in Example 3 and the multiple mutant obtained in Example 4 hardly decreases. It can be seen from these results that the multiple mutant obtained in Example 3 and the multiple mutant obtained in Example 4 are more stable to heat than WT.

Based on the result shown in FIG. 5, the temperature $T_{50}$ which is required to decrease the initial activity of each of the multiple mutant obtained in Example 3, the multiple mutant obtained in Example 4 and WT, to 50% by 10 minutes of incubation was calculated. In addition, based on the result shown in FIG. 5, the activation energy ($E_a$) of the thermal inactivation of each of the multiple mutant obtained in Example 3, the multiple mutant obtained in Example 4 and WT was calculated. It can be seen from these results that the multiple mutant obtained in Example 3 and the multiple mutant obtained in Example 4 are more stable than WT.

Test Example 5

To a tube for PCR, 12 µL of water, 2 µL of 10× a reverse transcriptase buffer {composition: 250 mM Tris hydrochloride buffer (pH 8.3) and 500 mM potassium chloride, 20 mM dithiothreitol}, 1 µL of 2.0 mM dNTP mixture, 1 µL of 10 µM RV-R26 primer aqueous solution, 1 µL of a standard RNA solution (1.6 pg/µL), 1 µL of an E. coli RNA solution (1.0 µg/µL), and 2 µL of an enzyme solution {composition of the solvent used in the enzyme solution: 10 mM potassium phosphate buffer (pH 7.6), 2 mM dithiothreitol, 0.2% by volume Triton™ X-100, and 10% by volume glycerol} of the multiple mutant obtained in Example 3, the multiple mutant obtained in Example 4 or WT (Comparative Example 1) were charged, and mixed, to prepare 20 µL of a reaction mixture solution.

As the standard RNA, an RNA having 1014 nucleotides corresponding to DNA sequences 8353 to 9366 of cesA gene (GenBank accession number: DQ360825) of *Bacillus cereus* was prepared by in vitro transcription. The nucleotide sequence and SEQ ID NO of RV-R26 primer are shown in Table 5.

TABLE 5

| Primer | Nucleotide Sequence | SEQ ID NO |
|---|---|---|
| RV-R26 | 5'-TGTGGAATTGTGAGCGGTGTCGCAATCACCGTAACACGACGTAG-3' | 3 |
| F5 | 5'-TGCGCGCAAAATGGGTATCAC-3' | 4 |
| RV | 5'-TGTGGAATTGTGAGCGG-3' | 5 |

The resulting reaction mixture solution was incubated at 46 to 64° C. for 30 minutes, and then heated at 95° C. for 5 minutes. Subsequently, 3 µL of the resulting product, 18 µL of water, 3 µL of 10×PCR buffer {composition: 500 mM potassium chloride, 100 mM Tris hydrochloride buffer (pH 8.3), and 15 mM magnesium chloride}, 1 µL of 10 µM F5 primer aqueous solution, 1 µL of 10 µM RV primer aqueous solution, 3 µL of 2.0 mM dNTP mixture, and 1 µL of a recombinant Taq polymerase solution {manufactured by TOYOBO CO., LTD., 1 U/µL} were mixed, to prepare 30 µL of a mixture for PCR. Using the resulting mixture for PCR, PCR was performed. PCR was performed by incubation at 95° C. for 30 seconds, followed by 30 cycles of reactions, each cycle being 95° C. for 30 seconds, 55° C. for 30 seconds and 72° C. for 30 seconds. The nucleotide sequence and SEQ ID NO of each of F5 primer and RB primer are as shown in Table 5.

The resulting amplified product was separated by electrophoresis using 1.0% by mass agarose gel, and stained with ethidium bromide (1 µg/mL). The result of performing electrophoresis in Test Example 5 is shown in FIG. 6.

Figure 6:
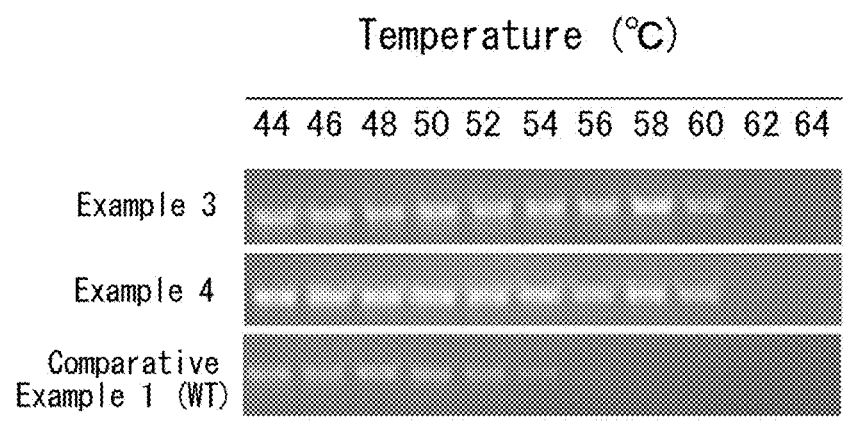
FIG. 6 is a drawing-substituting photograph showing the result of performing electrophoresis in Test Example 5.

It can be seen from the result shown in FIG. 6 that the highest temperature where the multiple mutant obtained in Example 3 and the multiple mutant obtained in Example 4 show a cDNA synthesis activity is 60° C., and the highest temperature where WT (Comparative Example) shows cDNA synthesis activity is 54° C. It can be seen from these results that the multiple mutant obtained in Example 3 and the multiple mutant obtained in Example 4 show cDNA synthesis activity at a higher temperature than WT.

Example 5

From the mutants with the amino acid residues to be substituted which were evaluated as AA in Test Example 1 substituted with other amino acid residues, three types of mutants (L435R, D124R, and E286R) were selected, in order of high remaining activity, excluding E302K.

The same procedures as in Production Example 2 were carried out except that primers designed so as to generate the substitution of the selected three amino acid residues were used in place of primers designed so as to generate the substitution of amino acid residues shown in Table 1 in Production Example 2, to give a multiple mutant of MMLV reverse transcriptase (D124R/E286R/L435R). As the result of SDS-PAGE analysis, the resulting multiple mutant was confirmed to show a single band of 75 kDa.

The score of magnitude of effective charge in the DNA interaction region of the resulting multiple mutant was +11.

Example 6

The same procedures as in Example 5 were carried out except that primers designed so as to generate the substitutions of the selected three amino acid residues and the substitution of Asp at position 524 with Ala (D524A) in SEQ ID NO.: 2 were used as primers for site-directed mutation in Example 5, to give a multiple mutant of MMLV reverse transcriptase (D124R/E286R/L435R/D524A). As the result of SDS-PAGE analysis, the resulting multiple mutant was confirmed to show a single band of 75 kDa.

The score of magnitude of effective charge in the DNA interaction region of the resulting multiple mutant was +11.

Example 7

The same procedures as in Example 5 were carried out except that primers designed so as to generate the two amino acid residue substitutions including L435R and E286R were used as primers for site-directed mutation in Example 5, to give a multiple mutant of MMLV reverse transcriptase (E286R/L435R). As the result of SDS-PAGE analysis, the resulting multiple mutant was confirmed to show a single band of 75 kDa.

The score of magnitude of effective charge in the DNA interaction region of the resulting multiple mutant was +9.

Example 8

The same procedures as in Example 5 were carried out except that primers designed so as to generate the substitution of the two amino acid residues selected in Example 7 and D524A were used as a primer for site-directed mutation in Example 5, to give a multiple mutant of MMLV reverse transcriptase (E286R/L435R/D524A). As the result of SDS-PAGE analysis, the resulting multiple mutant was confirmed to show a single band of 75 kDa.

The score of magnitude of effective charge in the DNA interaction region of the resulting multiple mutant was +9.

Test Example 6

Figure 7:
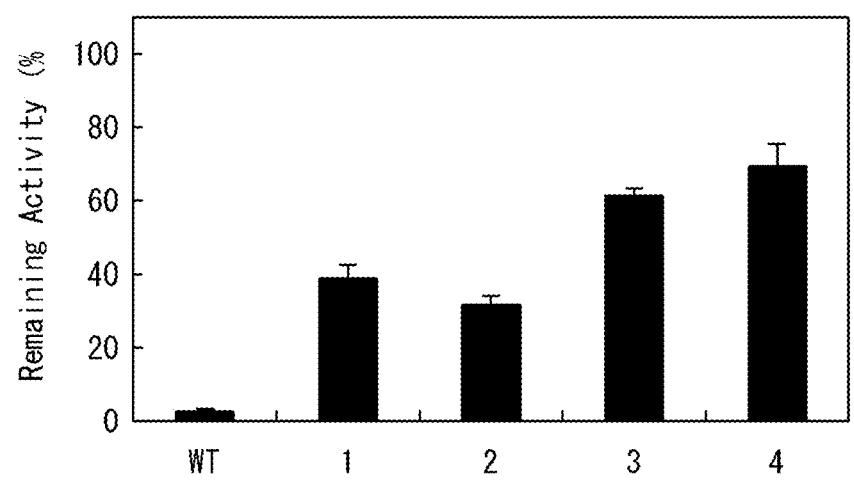
FIG. 7 is a graph showing the result of examining the relationship between the type of multiple mutant and a remaining activity of the multiple mutant in the presence of a template primer.

The same procedures as in Test Example 1 were carried out except that the multiple mutants obtained in Examples 5 to 8 were used in place of the single mutant obtained in Production Example 2 in Test Example 1, to calculate a remaining activity. The result of examining the relationship between the type of multiple mutant and a remaining activity of the multiple mutant in the presence of a template primer in Test Example 6 is shown in FIG. 7. In the figure, 1 shows a remaining activity of the multiple mutant obtained in Example 5, 2 shows a remaining activity of the multiple mutant obtained in Example 6, 3 shows a remaining activity of the multiple mutant obtained in Example 7, and 4 shows a remaining activity of the multiple mutant obtained in Example 8.

It can be seen from the result shown in FIG. 7 that the multiple mutants obtained in Examples 5 to 8 have a remarkably high thermal stability as compared to WT. Therefore, it can be seen from these results that high thermal stability can be ensured by substituting at least E286 with a positively-charged amino acid residue or a nonpolar amino acid residue in the region related to the interaction with a template primer in WT (the region corresponding to a threonine residue at position 24 to a proline residue at position 474 in the amino acid sequence shown in SEQ ID NO.: 2).

It can be seen from the above results that a mutant reverse transcriptase having high thermal stability is obtained by substituting at least E286 with a positively-charged amino acid residue or a nonpolar amino acid residue, in the region related to the interaction with a template primer in a wild-type MMLV reverse transcriptase (the region corresponding to a threonine residue at position 24 to a proline residue at position 474 in the amino acid sequence shown in SEQ ID NO.: 2).

Therefore, it can be seen that high thermal stability can be ensured by substituting the amino acid residue in the DNA interaction region with a positively-charged amino acid residue or a nonpolar amino acid residue to locate the positively-charged amino acid residue or the nonpolar amino acid residue in the DNA interaction region, such that the score of magnitude of effective charge of the DNA interaction region is larger than the effective charge in the DNA interaction region of WT.

Since the mutant reverse transcriptase described above (the mutant reverse transcriptase of the present invention) has high thermal stability, even when used in the reaction at high reaction temperature, high reverse transcription activity is exhibited. Thus, according to the mutant reverse transcriptase of the present invention, even when RNA used as a template contains a sequence likely to form secondary structure, the reaction temperature upon reverse transcription is set on a high temperature, thereby suppressing the formation of secondary structure and performing reverse transcription.

Therefore, it is suggested that the mutant reverse transcriptase of the present invention is useful as a versatile reagent for analysis (for example, kit for reverse transcription) that is not limited by the RNA containing sample used, a reagent for detecting virus, bacteria, diseases (for example, detection kit), or the like.

In a nucleic acid-related enzyme containing a reverse transcriptase, a nucleic acid interaction region interacting with a nucleic acid (a DNA interaction region in a reverse transcriptase) is present. Therefore, just like the mutant reverse transcriptase of the present invention, it is expected that high thermal stability can be ensured by substituting an amino acid residue in a nucleic acid interaction region with a positively-charged amino acid residue or a nonpolar amino acid residue.

Formulation Examples

Hereinafter, examples of a kit for reverse transcription and a detection kit are shown.
(Kit for Reverse Transcription)
  Mutant Reverse Transcriptase Obtained in Example 1
  10× Reverse Transcriptase Buffer
    {Composition: 250 mM Tris hydrochloride Buffer (pH 8.3), 500 mM Potassium Chloride, and 20 mM Dithiothreitol}
  2.0 mM dNTP Mixture
  10 µM Primer Aqueous Solution
  Standard RNA Solution (1.6 pg/µL)
(Detection Kit)
  Mutant Reverse Transcriptase Obtained in Example 1
  10× Reverse Transcriptase Buffer
    {Composition: 250 mM Tris hydrochloride Buffer (pH 8.3), 500 mM Potassium Chloride, and 20 mM Dithiothreitol}
  2.0 mM dNTP Mixture
  10 µM RV-R26 Primer Aqueous Solution
  Standard RNA Solution (1.6 pg/µL)
  E. coli RNA Solution (1.0 µg/µL)
Sequence Listing Free Text
  SEQ ID NO.: 3 is a sequence of RV-R26 primer.
  SEQ ID NO.: 4 is a sequence of F5 primer.
  SEQ ID NO.: 5 is a sequence of RV primer.

The invention claimed is:

1. A mutant reverse transcriptase comprising:
a DNA interaction region having a substitution of an amino acid residue corresponding to at least one of an aspartate residue at position 124 and a glutamate residue at position 286, such that either the aspartate residue at position 124, the glutamate residue at osition 286 or both the as sartate residue at position 124 and the glutamate residue at position 286 are substituted, in a DNA interaction region of a wild-type reverse transcriptase wherein the substitution or substitutions are that of a positively-charged amino acid residue or a nonpolar amino acid residue for the original negatively-charged amino acid residue or residues, and such that the mutant reverse transcriptase has a positive effective charge larger than that of the DNA interaction region in the wild-type reverse transcriptase,
wherein the wild-type reverse transcriptase comprises an amino acid sequence corresponding to SEQ ID NO: 2, and
wherein the mutant reverse transcriptase exhibits a reverse transcriptase activity.

2. The mutant reverse transcriptase according to claim 1, further comprising an amino acid sequence having a substitution of a residue corresponding to at least one of the amino acid residues in SEQ ID NO: 2:
a glutamate residue at position 69,
an aspartate residue at position 108,
a glutamate residue at position 117,
a glutamate residue at position 302,
a tryptophan residue at position 313,
a leucine residue at position 435, and
an asparagine residue at position 454,
with a positively-charged amino acid residue or a nonpolar amino acid residue, in an amino acid sequence corresponding to SEQ ID NO: 2, with the proviso that substitution of a glutamate residue at position 302 with an arginine residue is excluded,
wherein a score of magnitude of effective charge of a DNA interaction region in the amino acid sequence corresponding to SEQ ID NO: 2 is +11 to +13, the score of magnitude of effective charge being represented as the formula (I):

$$(+1 \times k) + (+1 \times r) + (-1 \times d) + (-1 \times e) \qquad (I),$$

wherein k represents the number of lysine residues, r represents the number of arginine residues, d represents the number of aspartate residues, and e represents the number of glutamate residues, and
wherein the mutant reverse transcriptase exhibits a reverse transcriptase activity.

3. The mutant reverse transcriptase according to claim 2, comprising an amino acid sequence having at least one of the following substitutions:
a substitution of a residue corresponding to a glutamate residue at position 286 SEQ ID NO: 2 with an alanine residue, a lysine residue or an arginine residue, and a substitution of a residue corresponding to an aspartate residue at position 124 of SEQ ID NO: 2 with an alanine residue, a lysine residue or an arginine residue,
and at least one substitution selected from the group consisting of a substitution of a residue corresponding to a glutamate residue at position 302 of SEQ ID NO: 2 with an alanine residue or a lysine residue,
a substitution of a residue corresponding to a residue at position 435 of SEQ ID NO: 2 with an alanine residue, a lysine residue or an arginine residue,
a substitution of a residue corresponding to a glutamate residue at position 69 of SEQ ID NO: 2 with an alanine residue or an arginine residue,
a substitution of a residue corresponding to an aspartate residue at position 108 of SEQ ID NO: 2 with an alanine residue, a lysine residue or an arginine residue,
a substitution of a residue corresponding to a glutamate residue at position 117 of SEQ ID NO: 2 with an alanine residue or a lysine residue,
a substitution of a residue corresponding to a tryptophan residue at position 313 of SEQ ID NO: 2 with an alanine residue, a lysine residue or an arginine residue, and
a substitution of a residue corresponding to an asparagine residue at position 454 of SEQ ID NO: 2 with an alanine residue or an arginine residue, in an amino acid sequence corresponding to SEQ ID NO: 2, wherein the mutant reverse transcriptase exhibits a reverse transcriptase activity.

4. The mutant reverse transcriptase according to claim 3, comprising:
(I) an amino acid sequence having the following substitutions of the amino acid residue (a-1) to (c-1):
(a-1) a substitution of a residue corresponding to a glutamate residue at position 286 of SEQ ID NO: 2 with an alanine residue,
(b-1) a substitution of a residue corresponding to a glutamate residue at position 302 of SEQ ID NO: 2 with a lysine residue, and
(c-1) a substitution of a residue corresponding to a leucine residue at position 435 of SEQ ID NO: 2 with an arginine residue, in an amino acid sequence corresponding to SEQ ID NO:2, or
(II) an amino acid sequence further comprising the following substitution:
(d-1) a substitution of a residue corresponding to an asparagine residue at position 124 of SEQ ID NO: 2 with an arginine residue, in the amino acid sequence of the item (I),
wherein the mutant reverse transcriptase exhibits a reverse transcriptase activity.

5. The mutant reverse transcriptase according to claim 4, comprising an amino acid sequence further comprising the following substitution:
(e-1) a substitution of a residue corresponding to an aspartate residue at position 524 of SEQ ID NO: 2 with an alanine residue, in the amino acid sequence of the item (I) or (II),
wherein the mutant reverse transcriptase exhibits a reverse transcriptase activity.

6. The mutant reverse transcriptase according to claim 1, wherein the mutant reverse transcriptase has a conserved substitution of an amino acid residue within a region corresponding to a threonine residue at position 24 to a proline residue at position 474 of SEQ ID NO: 2, in an amino acid sequence corresponding to SEQ ID NO: 2.

7. The mutant reverse transcriptase according to claim 1, wherein the mutant reverse transcriptase comprises any one of the following amino acid sequences:
(A) an amino acid sequence further comprising substitution, deletion, insertion or addition of one or several amino acid residues within an amino acid sequence corresponding to SEQ ID NO: 2 except for a region corresponding to a threonine residue at position 24 to a proline residue at position 474 of SEQ ID NO: 2, and
(B) an amino acid sequence having at least 80% sequence identity, the sequence identity being obtained by aligning the amino acid sequence with a sequence except for a region corresponding to a threonine residue at position 24 to a proline residue at position 474 in SEQ ID NO: 2, with the use of BLAST algorithm under conditions of Gap Costs (Existence 11 and Extension 1), Expect 10 and Word Size 3,
wherein the mutant reverse transcriptase exhibits a reverse transcriptase activity.

8. A nucleic acid encoding the mutant reverse transcriptase of claim 1.

9. A method for producing the mutant reverse transcriptase of claim 1, comprising the steps of:
culturing a cell harboring a nucleic acid encoding the mutant reverse transcriptase to express the reverse transcriptase encoded by the nucleic acid, thereby giving a culture, and collecting the mutant reverse transcriptase from the culture obtained in the above step.

10. A method for reverse transcription, comprising synthesizing cDNA from RNA with the use of the mutant reverse transcriptase of claim 1.

11. A kit for performing a reverse transcription, comprising the mutant reverse transcriptase of claim 1.

12. A kit for detecting a marker in a sample containing RNA obtained from a living body, comprising the mutant reverse transcriptase of claim 1 and a reagent for detecting the marker.

* * * * *

SEQUENCE LISTING

```
<160> NUMBER OF SEQ ID NOS: 5

<210> SEQ ID NO 1
<211> LENGTH: 2034
<212> TYPE: DNA
<213> ORGANISM: Moloney murine leukemia virus
<220> FEATURE:
<221> NAME/KEY: CDS
<222> LOCATION: (1)..(2034)

<400> SEQUENCE: 1 acc cta aat ata gaa gat gag cat cgg cta cat gag acc tca aaa gag      48
```

```
Thr Leu Asn Ile Glu Asp Glu His Arg Leu His Glu Thr Ser Lys Glu
1               5                   10                  15 cca gat gtt tct cta ggg tcc aca tgg ctg tct gat ttt cct cag gcc    96
Pro Asp Val Ser Leu Gly Ser Thr Trp Leu Ser Asp Phe Pro Gln Ala
                20                  25                  30 tgg gcg gaa acc ggg ggc atg gga ctg gca gtt cgc caa gct cct ctg   144
Trp Ala Glu Thr Gly Gly Met Gly Leu Ala Val Arg Gln Ala Pro Leu
            35                  40                  45 atc ata cct ctg aaa gca acc tct acc ccc gtg tcc ata aaa caa tac   192
Ile Ile Pro Leu Lys Ala Thr Ser Thr Pro Val Ser Ile Lys Gln Tyr
        50                  55                  60 ccc atg tca caa gaa gcc aga ctg ggg atc aag ccc cac ata cag aga   240
Pro Met Ser Gln Glu Ala Arg Leu Gly Ile Lys Pro His Ile Gln Arg
65                  70                  75                  80 ctg ttg gac cag gga ata ctg gta ccc tgc cag tcc ccc tgg aac acg   288
Leu Leu Asp Gln Gly Ile Leu Val Pro Cys Gln Ser Pro Trp Asn Thr
                85                  90                  95 ccc ctg cta ccc gtt aag aaa cca ggg act aat gat tat agg cct gtc   336
Pro Leu Leu Pro Val Lys Lys Pro Gly Thr Asn Asp Tyr Arg Pro Val
            100                 105                 110 cag gat ctg aga gaa gtc aac aag cgg gtg gaa gac atc cac ccc acc   384
Gln Asp Leu Arg Glu Val Asn Lys Arg Val Glu Asp Ile His Pro Thr
        115                 120                 125 gtg ccc aac cct tac aac ctc ttg agc ggg ctc cca ccg tcc cac cag   432
Val Pro Asn Pro Tyr Asn Leu Leu Ser Gly Leu Pro Pro Ser His Gln
130                 135                 140 tgg tac act gtg ctt gat tta aag gat gcc ttt ttc tgc ctg aga ctc   480
Trp Tyr Thr Val Leu Asp Leu Lys Asp Ala Phe Phe Cys Leu Arg Leu
145                 150                 155                 160 cac ccc acc agt cag cct ctc ttc gcc ttt gag tgg aga gat cca gag   528
His Pro Thr Ser Gln Pro Leu Phe Ala Phe Glu Trp Arg Asp Pro Glu
                165                 170                 175 atg gga atc tca gga caa ttg acc tgg acc aga ctc cca cag ggt ttc   576
Met Gly Ile Ser Gly Gln Leu Thr Trp Thr Arg Leu Pro Gln Gly Phe
            180                 185                 190 aaa aac agt ccc acc ctg ttt gat gag gca ctg cac aga gac cta gca   624
Lys Asn Ser Pro Thr Leu Phe Asp Glu Ala Leu His Arg Asp Leu Ala
        195                 200                 205 gac ttc cgg atc cag cac cca gac ttg atc ctg cta cag tac gtg gat   672
Asp Phe Arg Ile Gln His Pro Asp Leu Ile Leu Leu Gln Tyr Val Asp
210                 215                 220 gac tta ctg ctg gcc gcc act tct gag cta gac tgc caa caa ggt act   720
Asp Leu Leu Leu Ala Ala Thr Ser Glu Leu Asp Cys Gln Gln Gly Thr
225                 230                 235                 240 cgg gcc ctg tta caa acc cta ggg aac ctc ggg tat cgg gcc tcg gcc   768
Arg Ala Leu Leu Gln Thr Leu Gly Asn Leu Gly Tyr Arg Ala Ser Ala
                245                 250                 255 aag aaa gcc caa att tgc cag aaa cag gtc aag tat ctg ggg tat ctt   816
Lys Lys Ala Gln Ile Cys Gln Lys Gln Val Lys Tyr Leu Gly Tyr Leu
            260                 265                 270 cta aaa gag ggt cag aga tgg ctg act gag gcc aga aaa gag act gtg   864
Leu Lys Glu Gly Gln Arg Trp Leu Thr Glu Ala Arg Lys Glu Thr Val
        275                 280                 285 atg ggg cag cct act ccg aag acc cct cga caa cta agg gag ttc cta   912
Met Gly Gln Pro Thr Pro Lys Thr Pro Arg Gln Leu Arg Glu Phe Leu
290                 295                 300 ggg acg gca ggc ttc tgt cgc ctc tgg atc cct ggg ttt gca gaa atg   960
Gly Thr Ala Gly Phe Cys Arg Leu Trp Ile Pro Gly Phe Ala Glu Met
305                 310                 315                 320
```

-continued

| | | |
|---|---|---|
| gca gcc ccc ttg tac cct ctc acc aaa acg ggg act ctg ttt aat tgg<br>Ala Ala Pro Leu Tyr Pro Leu Thr Lys Thr Gly Thr Leu Phe Asn Trp<br>                        325                    330                  335 | 1008 |
| ggc cca gac caa caa aag gcc tat caa gaa atc aag caa gct ctt cta<br>Gly Pro Asp Gln Gln Lys Ala Tyr Gln Glu Ile Lys Gln Ala Leu Leu<br>                    340                    345                    350 | 1056 |
| act gcc cca gcc ctg ggg ttg cca gat ttg act aag ccc ttt gaa ctc<br>Thr Ala Pro Ala Leu Gly Leu Pro Asp Leu Thr Lys Pro Phe Glu Leu<br>               355                    360                    365 | 1104 |
| ttt gtc gac gag aag cag ggc tac gcc aaa ggt gtc cta acg caa aaa<br>Phe Val Asp Glu Lys Gln Gly Tyr Ala Lys Gly Val Leu Thr Gln Lys<br>370                    375                    380 | 1152 |
| ctg gga cct tgg cgt cgg ccg gtg gcc tac ctg tcc aaa aag cta gac<br>Leu Gly Pro Trp Arg Arg Pro Val Ala Tyr Leu Ser Lys Lys Leu Asp<br>385                    390                    395                    400 | 1200 |
| cca gta gca gct ggg tgg ccc cct tgc cta cgg atg gta gca gcc att<br>Pro Val Ala Ala Gly Trp Pro Pro Cys Leu Arg Met Val Ala Ala Ile<br>                          405                    410                    415 | 1248 |
| gcc gta ctg aca aag gat gca ggc aag cta acc atg gga cag cca cta<br>Ala Val Leu Thr Lys Asp Ala Gly Lys Leu Thr Met Gly Gln Pro Leu<br>                    420                    425                    430 | 1296 |
| gtc att ctg gcc ccc cat gca gta gag gca cta gtc aaa caa ccc ccc<br>Val Ile Leu Ala Pro His Ala Val Glu Ala Leu Val Lys Gln Pro Pro<br>               435                    440                    445 | 1344 |
| gac cgc tgg ctt tcc aac gcc cgg atg act cac tat cag gcc ttg ctt<br>Asp Arg Trp Leu Ser Asn Ala Arg Met Thr His Tyr Gln Ala Leu Leu<br>                          450                    455                    460 | 1392 |
| ttg gac acg gac cgg gtc cag ttc gga ccg gtg gta gcc ctg aac ccg<br>Leu Asp Thr Asp Arg Val Gln Phe Gly Pro Val Val Ala Leu Asn Pro<br>465                    470                    475                    480 | 1440 |
| gct acg ctg ctc cca ctg cct gag gaa ggg ctg caa cac aac tgc ctt<br>Ala Thr Leu Leu Pro Leu Pro Glu Glu Gly Leu Gln His Asn Cys Leu<br>                          485                    490                    495 | 1488 |
| gat atc ctg gcc gaa gcc cac gga acc cga ccc gac cta acg gac cag<br>Asp Ile Leu Ala Glu Ala His Gly Thr Arg Pro Asp Leu Thr Asp Gln<br>                    500                    505                    510 | 1536 |
| ccg ctc cca gac gcc gac cac acc tgg tac acg gat gga agc agt ctc<br>Pro Leu Pro Asp Ala Asp His Thr Trp Tyr Thr Asp Gly Ser Ser Leu<br>               515                    520                    525 | 1584 |
| tta caa gag gga cag cgt aag gcg gga gct gcg gtg acc acc gag acc<br>Leu Gln Glu Gly Gln Arg Lys Ala Gly Ala Ala Val Thr Thr Glu Thr<br>530                    535                    540 | 1632 |
| gag gta atc tgg gct aaa gcc ctg cca gcc ggg aca tcc gct cag cgg<br>Glu Val Ile Trp Ala Lys Ala Leu Pro Ala Gly Thr Ser Ala Gln Arg<br>545                    550                    555                    560 | 1680 |
| gct gaa ctg ata gca ctc acc cag gcc cta aag atg gca gaa ggt aag<br>Ala Glu Leu Ile Ala Leu Thr Gln Ala Leu Lys Met Ala Glu Gly Lys<br>                    565                    570                    575 | 1728 |
| aag cta aat gtt tat act gat agc cgt tat gct ttt gct act gcc cat<br>Lys Leu Asn Val Tyr Thr Asp Ser Arg Tyr Ala Phe Ala Thr Ala His<br>               580                    585                    590 | 1776 |
| atc cat gga gaa ata tac aga agg cgt ggg ttg ctc aca tca gaa ggc<br>Ile His Gly Glu Ile Tyr Arg Arg Arg Gly Leu Leu Thr Ser Glu Gly<br>               595                    600                    605 | 1824 |
| aaa gag atc aaa aat aaa gac gag atc ttg gcc cta cta aaa gcc ctc<br>Lys Glu Ile Lys Asn Lys Asp Glu Ile Leu Ala Leu Leu Lys Ala Leu<br>610                    615                    620 | 1872 |
| ttt ctg ccc aaa aga ctt agc ata atc cat tgt cca gga cat caa aag<br>Phe Leu Pro Lys Arg Leu Ser Ile Ile His Cys Pro Gly His Gln Lys<br>625                    630                    635                    640 | 1920 |

-continued

```
gga cac agc gcc gag gct aga ggc aac cgg atg gct gac caa gcg gcc    1968
Gly His Ser Ala Glu Ala Arg Gly Asn Arg Met Ala Asp Gln Ala Ala
            645                 650                 655 cga aag gca gcc atc aca gag act cca gac acc tct acc ctc ctc cac    2016
Arg Lys Ala Ala Ile Thr Glu Thr Pro Asp Thr Ser Thr Leu Leu His
        660                 665                 670 cac cac cat cac cac tag                                             2034
His His His His His
        675
```

<210> SEQ ID NO 2
<211> LENGTH: 677
<212> TYPE: PRT
<213> ORGANISM: Moloney murine leukemia virus

<400> SEQUENCE: 2

```
Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
```

```
            305                 310                 315                 320
        Ala Ala Pro Leu Tyr Pro Leu Thr Lys Thr Gly Thr Leu Phe Asn Trp
                        325                 330                 335

Gly Pro Asp Gln Gln Lys Ala Tyr Gln Glu Ile Lys Gln Ala Leu Leu
                        340                 345                 350

Thr Ala Pro Ala Leu Gly Leu Pro Asp Leu Thr Lys Pro Phe Glu Leu
                        355                 360                 365

Phe Val Asp Glu Lys Gln Gly Tyr Ala Lys Val Leu Thr Gln Lys
                370                 375                 380

Leu Gly Pro Trp Arg Arg Pro Val Ala Tyr Leu Ser Lys Lys Leu Asp
        385                 390                 395                 400

Pro Val Ala Ala Gly Trp Pro Pro Cys Leu Arg Met Val Ala Ile
                                405                 410                 415

Ala Val Leu Thr Lys Asp Ala Gly Lys Leu Thr Met Gly Gln Pro Leu
                        420                 425                 430

Val Ile Leu Ala Pro His Ala Val Glu Ala Leu Val Lys Gln Pro Pro
                        435                 440                 445

Asp Arg Trp Leu Ser Asn Ala Arg Met Thr His Tyr Gln Ala Leu Leu
                450                 455                 460

Leu Asp Thr Asp Arg Val Gln Phe Gly Pro Val Val Ala Leu Asn Pro
        465                 470                 475                 480

Ala Thr Leu Leu Pro Leu Pro Glu Glu Gly Leu Gln His Asn Cys Leu
                        485                 490                 495

Asp Ile Leu Ala Glu Ala His Gly Thr Arg Pro Asp Leu Thr Asp Gln
                        500                 505                 510

Pro Leu Pro Asp Ala Asp His Thr Trp Tyr Thr Asp Gly Ser Ser Leu
                        515                 520                 525

Leu Gln Glu Gly Gln Arg Lys Ala Gly Ala Ala Val Thr Thr Glu Thr
                        530                 535                 540

Glu Val Ile Trp Ala Lys Ala Leu Pro Ala Gly Thr Ser Ala Gln Arg
        545                 550                 555                 560

Ala Glu Leu Ile Ala Leu Thr Gln Ala Leu Lys Met Ala Glu Gly Lys
                        565                 570                 575

Lys Leu Asn Val Tyr Thr Asp Ser Arg Tyr Ala Phe Ala Thr Ala His
                        580                 585                 590

Ile His Gly Glu Ile Tyr Arg Arg Arg Gly Leu Leu Thr Ser Glu Gly
                        595                 600                 605

Lys Glu Ile Lys Asn Lys Asp Glu Ile Leu Ala Leu Leu Lys Ala Leu
                610                 615                 620

Phe Leu Pro Lys Arg Leu Ser Ile Ile His Cys Pro Gly His Gln Lys
        625                 630                 635                 640

Gly His Ser Ala Glu Ala Arg Gly Asn Arg Met Ala Asp Gln Ala Ala
                        645                 650                 655

Arg Lys Ala Ala Ile Thr Glu Thr Pro Asp Thr Ser Thr Leu Leu His
                        660                 665                 670

His His His His His
                        675

<210> SEQ ID NO 3
<211> LENGTH: 44
<212> TYPE: DNA
<213> ORGANISM: Artificial
<220> FEATURE:
<223> OTHER INFORMATION: A sequence of RV-R

```
<400> SEQUENCE: 3
tgtggaattg tgagcggtgt cgcaatcacc gtaacacgac gtag        44

<210> SEQ ID NO 4
<211> LENGTH: 21
<212> TYPE: DNA
<213> ORGANISM: Artificial
<220> FEATURE:
<223> OTHER INFORMATION: A sequence of F5 primer

<400> SEQUENCE: 4
tgcgcgcaaa atgggtatca c                                 21

<210> SEQ ID NO 5
<211> LENGTH: 17
<212> TYPE: DNA
<213> ORGANISM: Artificial
<220> FEATURE:
<223> OTHER INFORMATION: A sequence of RV primer

<400> SEQUENCE: 5
tgtggaattg tgagcgg                                      17
```